(12) United States Patent
Kitamura et al.

(10) Patent No.: US 6,716,628 B2
(45) Date of Patent: Apr. 6, 2004

(54) CHONDROGENESIS PROMOTERS AND INDOLIN-2-ONE DERIVATIVES

(75) Inventors: Hidetomo Kitamura, Gotenba (JP); Atsuhiko Kato, Gotenba (JP); Toru Esaki, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 3 days.

(21) Appl. No.: 10/224,311

(22) Filed: Aug. 21, 2002

(65) Prior Publication Data

US 2003/0119896 A1 Jun. 26, 2003

Related U.S. Application Data

(63) Continuation of application No. 09/890,071, filed as application No. PCT/JP00/00381 on Jan. 26, 2000, now Pat. No. 6,500,854.

(30) Foreign Application Priority Data

Jan. 29, 1999 (JP) ......................... P11-057494
Aug. 19, 1999 (JP) ......................... P11-233172

(51) Int. Cl.$^7$ ................................. C12N 5/02
(52) U.S. Cl. ................ 435/384; 435/325; 435/383; 435/395
(58) Field of Search ................. 435/325, 383, 435/384, 395

(56) References Cited

U.S. PATENT DOCUMENTS

| | | | |
|---|---|---|---|
| 5,952,511 A | 9/1999 | Esaki et al. | 548/486 |
| 6,031,111 A | 2/2000 | Esaki et al. | 548/483 |
| 6,150,163 A | * 11/2000 | McPherson et al. | 435/384 |

FOREIGN PATENT DOCUMENTS

| | | |
|---|---|---|
| JP | 7-048349 | 2/1995 |
| JP | 9-328467 | 12/1997 |
| JP | 10-077230 | 3/1998 |
| WO | WO 94/19322 | 1/1994 |
| WO | WO 97/33867 | 9/1997 |
| WO | WO 98/02419 | 1/1998 |

OTHER PUBLICATIONS

Masayuki Azuma, et al., "Induction of Cells with a Chondrocyte–like Phenotype by Treatment with 1α, 25–Dihydroxyvitamin $D_3$ a Human Salivary Acinar Cell Line," Cancer Research, vol. 49, Oct. 1, 1989, pp. 5435–5442.

Warner M. Burch and Harold E. Lebovitz, "Triiodothyronine Stimulation of in Vitro Growth and Maturation of Embryonic Chick Cartilage," Endocrinology, vol. 111, No. 2, 1982, pp. 462–468.

Paul Dieppe, "Therapeutic Targets in Osteoarthritis," The Journal of Rheumatology, vol. 22:1, Supplement 43, 1995, pp. 136–139.

Harrie L. Glanbeek, et al., "Stimulation of Articular Cartilage Repair in Established Arthritis by Local Administration of Transforming Growth Factor–β into Murine Knee Joints," Laboratory Investigation, vol. 78, No. 2, Feb. 1998, pp. 133–142.

H. Ide and H. Aono, "Retinoic Acid Promotes Proliferation and Chondrogenesis in the Distal Mesodermal Cells of Chick Limb Bud," Development Biology, vol. 130, 1998, pp. 767–773.

Yukio Kato, et al., "Effect of Vanadate on Cartilage–Matrix Proteoglycan Synthesis in Rabbit Coastal Chondrocyte Cultures," The Journal of Cell Biology, vol. 104, Feb. 1987, pp. 311–319.

Lawrence Kent, Charles J. Malemud and Roland W. Moskowitz, "Differential Response of Articular Chondrocyte Populations to Thromboxane $B_2$ and Analogs of Prostaglandin Cyclic Endoperoxides," Prostaglandins, Vo. 19, No. 3, Mar. 1980, pp. 391–406.

H. Kitamura et al., "AG–041R, A Novel Indoline–2–One Derivative, Induces Systemic Cartilage Hyperplasia in Rats", Eur. J. Pharmacol, vol. 418, No. 3, 2001, pp. 225–230, XP002187328.

David J. McQuillan, et al., "The Relation of Protein Synthesis to Chondroitin Sulphate Biosynthesis in Cultured Bovine Cartilage," Biochem. J., vol. 224, 1984, pp. 977–988.

R. P. Miller, M. Husain, and S. Lohin, "Long Acting cAMP Analogues Enhance Sulfate Incorporation into Matrix Proteoglycans and Suppress Cell Division of Fetal Ral Chondrocytes in Monolayer Culture," J. Cell. Physiol., vol. 100, 1979, pp. 63–76.

(List continued on next page.)

Primary Examiner—Fiona T. Powers
(74) Attorney, Agent, or Firm—Morgan, Lewis & Bockius LLP

(57) ABSTRACT

A chondrogenesis promoter comprising as an active ingredient a compound represented by general formula (I) or a salt thereof:

(I)

wherein $R^1$ represents a halogen atom, a lower alkyl group, a lower alkoxy group, etc.; $R^2$ represents a hydrogen atom, a lower alkyl group, a lower alkenyl group, a lower alkynyl group, a lower alkoxy group, an acyl group, an aryl group, a heterocyclic group, etc.; $R^3$ represents a lower alkyl group, a cycloalkyl group, an aryl group, a heterocyclic group, etc.; $R^4$ represents a hydrogen atom, a lower alkyl group, an aryl group, a heterocyclic group, etc.; X and Y represent —$CH_2$—, —NH— or —O—; and n represents an integer of 0–4.

21 Claims, 18 Drawing Sheets

OTHER PUBLICATIONS

Shinobu Nakanishi and Edwin M. Uyeki, "Benzamide on Chondrocytic Differentiation in Chick Limb Bud Cell Culture," J. Embryol. exp. Morph., vol. 85, 1985, pp. 163–175.

Rani S. Sellers, Diane Peluso, and Elisabeth A. Morris, "The Effect of Recombinant Human Bone Morphogenectic Protein–2 (rhBMP–2) on the Healing of Full–Thickness Defects of Articular Cartilage," The Journal of Bone and Joint Surgery, vol. 79–A, No. 10, Oct. 1997, pp. 1452–1463.

Y. Shimomura, T. Yoneda, and F. Suzuki, "Osteogenesis by Chondrocytes from Growth Cartilage of Rat Rib," Calcif. Tiss. Res., vol. 19, 1975, pp. 179–187.

Henk M. Van Beuningen, et al., "Transforming Growth Factor–$\beta 1$ Stimulates Articular Chondrocyte Proteoglycan Synthesis and Includes Osteophyte Formation in the Murine Knee Joint," Laboratory Investigation, vol. 71, No. 2, 1994, pp. 279–290.

Shigeyuki Wakitani, et al., "Mesenchymal Cell–Based Repair of Large Full–Thichness Defects of Articular Cartilage", The Journal of Bone and Joint Surgery, vol. 76–A, No. 4, Apr. 1994, pp. 579–592.

Weiqun Yan, et al., "Stimulation by Concanavalin A of Cartilage–Matrix Proteoglycan Synthesis in Chondrocyte Cultures," The Journal of Biological Chemistry, vol. 265, No. 17, Jun. 15, 1990, pp. 10125–10131.

* cited by examiner

**: p<0.01 (Student t test)

**: p<0.01 (Student t test)

**: p<0.01
(nonparametric Dunnett multiple comparison)

- Cell morphology
- Matrix-staining
- Thickness of cartilage

- Total score

*: $p<0.01$
(Wilcoxon signed rank test)

\*\*: p<0.01
(non-corresponding Student t test)

*: $p<0.05$
(non-corresponding Student t test)

- ☐ Loss of superficial layer
- ▧ Ulceration or erosion
- ▨ Fibrillation
- ▩ Cluster formation ☐ Global assessment

*: $p<0.05$, **: $p<0.01$
(Wilcoxon signed rank test)

CHONDROGENESIS PROMOTERS AND INDOLIN-2-ONE DERIVATIVES

This application is a continuation of application Ser. No. 09/890,071, filed Sep. 21, 2001, now U.S. Pat. No. 6,500,854 which is the U.S. national phase of PCT International Application No. PCT/JP00/00381, filed Jan. 26, 2000, which claims priority to Japanese application Nos. P1999-057494, filed Jan. 29, 1999 and P1999-233172, filed Aug. 19, 1999.

TECHNICAL FIELD

The present invention relates to pharmaceutically useful indolin-2-one derivatives or their salts, and to chondrogenesis promoters, cartilage repair agents and cartilage diagnostic reagents containing the indolin-2-one derivatives or their pharmaceutically acceptable salts.

BACKGROUND ART

Cartilage in the body generally consists of chondrocytes and fibrocytes, which are specialized connective tissue cells, and an amorphous gel-like matrix in which they are embedded, and it forms a part of the supportive tissue of the body.

In warm-blooded animals including humans, cartilage forms the skeleton, joints, tracheae, auricula, nose and the like. That is, it performs a central role in functions that are indispensable to the survival of warm-blooded animals, including acting as a template for bone during growth (growth cartilage), and contributing to smooth joint movement (articular cartilage), respiration (tracheal cartilage, nasal cartilage) and hearing (auricular cartilage). Thus, degeneration or destruction of these types of cartilage causes various degrees of detriment to the body depending on the site and severity of degeneration or destruction.

For example, among the aforementioned functions in which cartilage plays a role (growth, joints, respiration, hearing, etc.), the smooth movement of joints is particularly impaired by degeneration or destruction of articular cartilage in such conditions as chronic rheumatoid arthritis or osteoarthritis. Degeneration or destruction of articular cartilage is believed to be the major cause of the walking difficulty that results from such diseases.

The prospect of suppressing articular degeneration or destruction or of promoting chondrogenesis has been raised as a possible method of treating conditions such as chronic rheumatoid arthritis and osteoarthritis (J. Rheum. 22(1), Suppl. 43:136–139, 1995, Lab. Invest. 78(2):133–142).

Several different organism-derived substances and low molecular substances are known to have effects of promoting chondrogenesis or of inducing proliferation of chondrocytes. Substances that have been reported to have chondrogenesis-promoting effects include growth factors such as TGF-β (Transforming growth factor β), BMP-2 (J. Bone Joint Surg. 79-A(10):1452–1463, 1997), concanavalin A which is a type of lectin (J. Biol. Chem., 265:10125–10131, 1990) and osteogenin (BMP-7), as well as low molecular substances such as vitamin D derivatives (1α, 25-$D_3$) (Cancer Res., 49:5435–5442, 1989), vitamin A derivatives (retinoic acid) (Dev. Biol., 130:767–773, 1988), vanadates (J. Cell Biol., 104:311–319, 1987), benzamides (J. Embryol. Exp. Morphol., 85:163–175, 1985), benzyl β-D-xyloside (Biochem. J., 224:977–988, 1984), triiodothyronines ($T_3$) (Endocrinology, 111:462–468, 1982), prostaglandin derivatives ($PGE_2$, U44069) (Prostaglandin, 19:391–406, 1980), dbcAMP (J. Cell. Physiol., 100:63–76, 1979) and 8-Br-cAMP(J. Cell. Physiol., 100:63–76, 1979).

Of these organism-derived substances and low molecular substances, TGF-β holds the most promise as a useful treatment agent, and TGF-$β_1$, which is one isoform of TGF-β, has been reported to promote chondrogenesis when intraarticularly administered (Lab. Invest. 71(2):279–290, 1994). Also, since TGF-$β_1$ suppresses arthritis-induced loss of proteoglycans in articular cartilage, or stated differently, it inhibits destruction of articular cartilage due to its anabolic effect on articular cartilage when administered intraarticularly in experimental animal models with induced arthritis, its possibility as a useful treatment agent for articular disease such as rheumatism has been suggested (Lab. Invest. 78(2): 133–142, 1998).

However, even TGF-β which holds the most promise as a useful treatment agent has been reported to provoke synovitis even while promoting chondrogenesis, and this therefore poses a serious problem for its use as a treatment agent for articular diseases (Lab. Invest. 71(2):279–290, 1994), for which reason it has not been applied in the clinic as a treatment agent for such conditions. In summary, then, no practical treatment agent therapy exists that is based on promoting chondrogenesis.

DISCLOSURE OF THE INVENTION

It is an object of the present invention to overcome the aforementioned drawbacks of the prior art by providing a chondrogenesis promoter and cartilage repair agent that are able to promote chondrogenesis or induce proliferation of chondrocytes.

It is another object of the invention to provide a reagent with chondrogenesis promoting action which is useful for biological, physical or chemical research on cartilage.

It is yet another object of the invention to provide indolin-2-one derivatives that are useful as chondrogenesis promoters.

It is still yet another object of the invention to provide indolin-2-one derivatives that are useful as bone fracture repair promoters.

As a result of diligent research aimed at achieving these objects, the present inventors have completed the present invention upon the discovery that indolin-2-one derivatives having a specific structure exhibit a chondrogenesis promoting effect.

In other words, a chondrogenesis promoter according to the invention comprises as an active ingredient a compound represented by general formula (I) or a salt thereof:

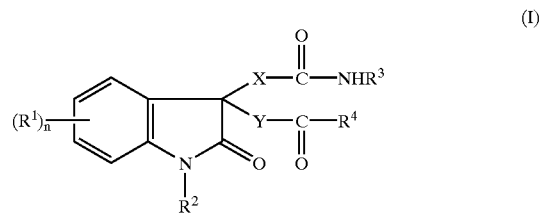

(I)

wherein
R$^1$ represents a halogen atom, a lower alkyl group, a lower alkoxy group, a hydroxyl group, a nitro group, a trifluoromethyl group, a lower alkylthio group, an acyl group, a carboxyl group, a mercapto group or an amino group with an optional substituent;
R$^2$ represents a hydrogen atom, a lower alkyl group with an optional substituent, a lower alkenyl group with an optional substituent, a lower alkynyl group with an optional substituent, a lower alkoxy group with an optional substituent, an acyl group with an optional substituent, an aryl group with an optional substituent or a heterocyclic group with an optional substituent;

$R^3$ represents a lower alkyl group with an optional substituent, a cycloalkyl group with an optional substituent, an aryl group with an optional substituent or a heterocyclic group with an optional substituent;

$R^4$ represents a hydrogen atom, a lower alkyl group with an optional substituent, an aryl group with an optional substituent, a heterocyclic group with an optional substituent, $-OR^5$, $-SR^5$ or $-NR^6R^7$ wherein $R^5$, $R^6$ and $R^7$ may be the same or different and each represents a hydrogen atom, a lower alkyl group with an optional substituent, a cycloalkyl group with an optional substituent, an aryl group with an optional substituent, a heterocyclic group with an optional substituent, a lower alkoxy group or an amino group with an optional substituent, and $R^6$ and $R^7$ may together form a group represented by $-(CH_2)_m-$ or $-(CH_2)_lNR^8(CH_2)_k-$ wherein k, l and m each represent an integer of 1–8 and $R^8$ represents a hydrogen atom or a lower alkyl group;

X and Y may be the same or different and each represents $-CH_2-$, $-NH-$ or $-O-$, and n represents an integer of 0–4.

A cartilage repair agent according to the invention also comprises as an active ingredient a compound represented by general formula (I) above or a salt thereof.

A reagent for biological, physical or chemical research on cartilage according to the invention also comprises as an active ingredient a compound represented by general formula (I) above or a salt thereof.

An indolin-2-one derivative according to the invention is represented by the following general formula (IV):

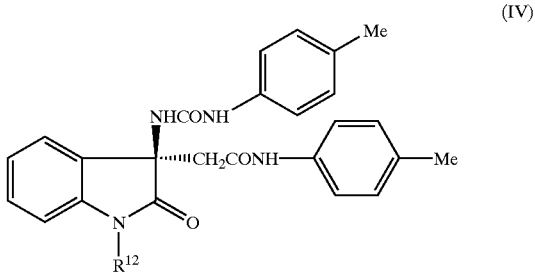

(IV)

wherein $R^{12}$ represents a lower alkyl group substituted at the same carbon with two lower alkoxy groups which is optionally substituted with 1–5 halogen atoms.

Also, $R^{12}$ of the indolin-2-one derivative according to the invention may be represented by general formula (V):

(V)

wherein $R^{13}$ and $R^{14}$ may be the same or different, and each represents a lower alkyl group which is optionally substituted with 1–5 halogen atoms.

BRIEF DESCRIPTION OF THE DRAWINGS

FIG. 13A shows the scores for cell morphology, matrix-staining and thickness of cartilage, and FIG. 13B shows the total scores.

FIG. 15A and FIG. 15B both contain photomicrographs of 6 individuals.

FIG. 16A shows the average area of mild lesions, FIG. 16B shows the average area of medium lesions and FIG. 16C shows the average of the total lesion area as the sum of the mild and medium lesion areas.

FIG. 17A shows the scores for loss of superficial layer, ulceration or erosion, fibrillation and cluster formation, and FIG. 17B shows the global assessment score.

BEST MODE FOR CARRYING OUT THE INVENTION

Figure 1A:
FIG. 1A is a photomicrograph showing a hematoxylin/eosin double stained auricular tissue sample from a rat after repeated oral administration of a vehicle control (3% gum Arabic) for 4 weeks.
Figure 1B:
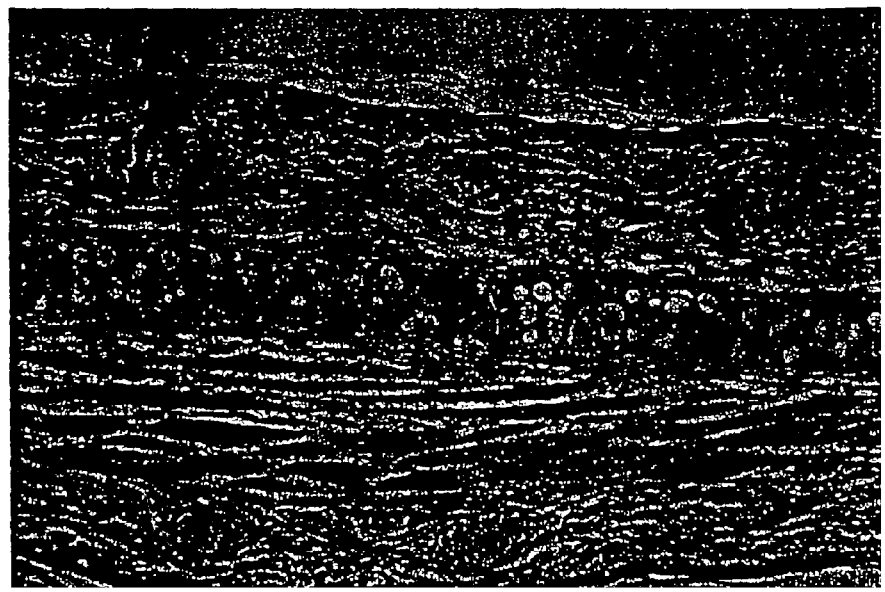
FIG. 1B is a photomicrograph showing a hematoxylin/eosin double stained auricular tissue sample from a rat after repeated oral administration of compound A (2 g/kg) for 4 weeks.
Figure 2A:
FIG. 2A is a photomicrograph showing a hematoxylin/eosin double stained trachea tissue sample from a rat after repeated oral administration of a vehicle control (3% gum Arabic) for 4 weeks.
Figure 2B:
FIG. 2B is a photomicrograph showing a hematoxylin/eosin double stained trachea tissue sample from a rat after repeated oral administration of compound A (2 g/kg) for 4 weeks.
Figure 3A:
FIG. 3A is a photomicrograph showing a hematoxylin/eosin double stained sternal xiphoid process tissue sample from a rat after repeated oral administration of a vehicle control (3% gum Arabic) for 4 weeks.
Figure 3B:
FIG. 3B is a photomicrograph showing a hematoxylin/eosin double stained sternal xiphoid process tissue sample from a rat after repeated oral administration of compound A (2 g/kg) for 4 weeks.
Figure 4A:
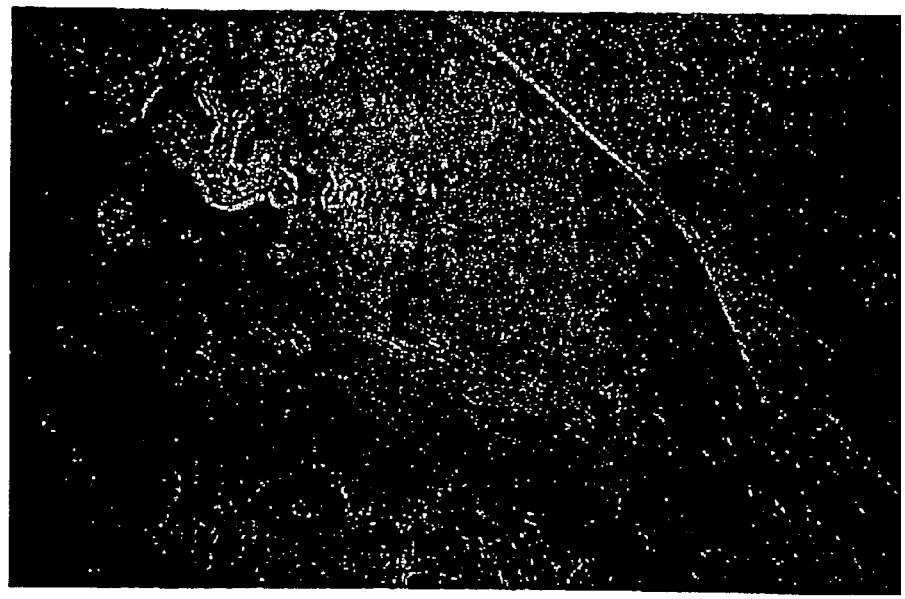
FIG. 4A is a photomicrograph showing a hematoxylin/eosin double stained knee joint tissue sample from a rat after repeated oral administration of a vehicle control (3% gum Arabic) for 4 weeks.
Figure 4B:
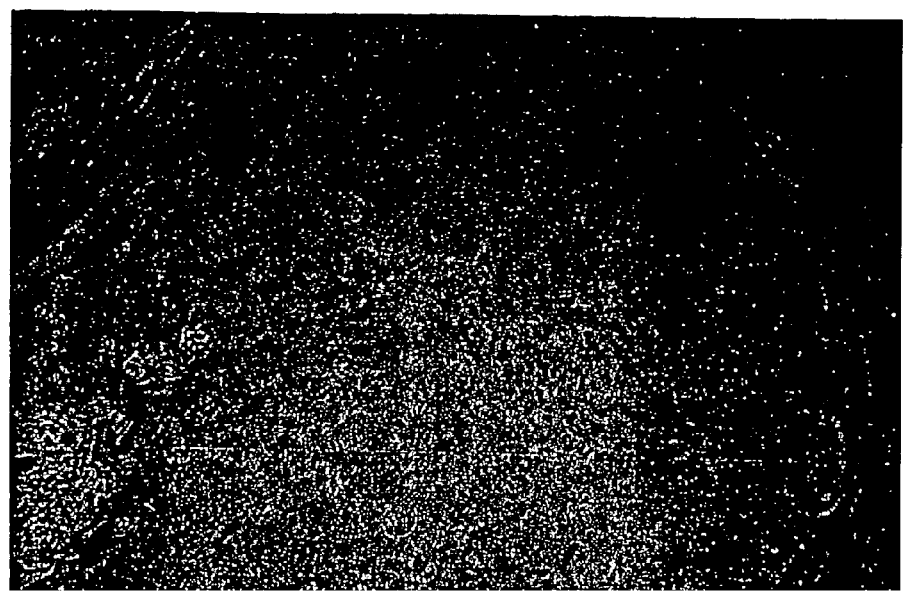
FIG. 4B is a photomicrograph showing a hematoxylin/eosin double stained knee joint tissue sample from a rat after repeated oral administration of compound A (2 g/kg) for 4 weeks.
Figure 5A:
FIG. 5A is a photomicrograph showing a hematoxylin/eosin double stained lumbar spine (disk) tissue sample from a rat after repeated oral administration of a vehicle control (3% gum Arabic) for 4 weeks.
Figure 5B:
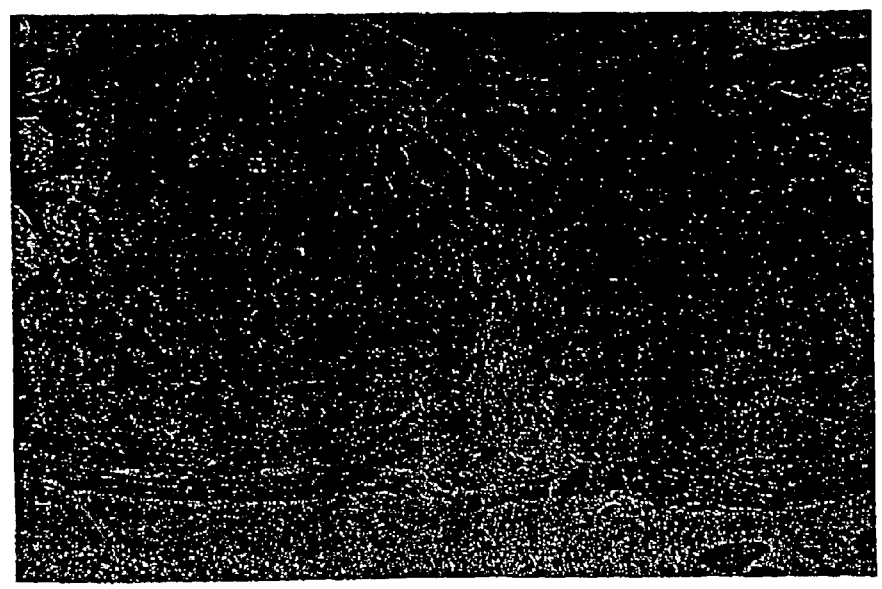
FIG. 5B is a photomicrograph showing a hematoxylin/eosin double stained lumbar spine (disk) tissue sample from a rat after repeated oral administration of compound A (2 g/kg) for 4 weeks.

The present invention will now be explained in greater detail with reference to the attached drawings as appropriate. The amounts indicated as "parts" and "%" values in the following explanations are based on weight unless otherwise specified.

A chondrogenesis promoter or cartilage repair agent according to the invention comprises as an active ingredient a compound represented by the aforementioned general formula (I) or a salt thereof.

Compounds represented by general formula (I) according to the invention are described in WO94/19322, and the same patent publication teaches that the compounds are CCK-B/gastrin receptor antagonists. The present inventors have found that compounds represented by general formula (I) have an unexpected chondrogenesis promoting effect, and the present invention has been completed on the basis of this discovery. The compounds represented by general formula (I) of the invention may be obtained by the method described in the aforementioned international patent publication, or by the method illustrated hereunder in the examples.

A "halogen atom" according to the invention is a fluorine atom, a chlorine atom, a bromine atom or an iodine atom.

A "lower alkyl group" according to the invention is a linear or branched alkyl group of 1 to 6 carbons, such as a methyl group, an ethyl group, a n-propyl group, an i-propyl group, a n-butyl group, a s-butyl group, a t-butyl group, a pentyl group, a hexyl group or the like.

A "lower alkenyl group" is a linear or branched alkenyl group of 2 to 6 carbons, such as a vinyl group, an allyl group, a butenyl group, a pentenyl group, a hexenyl group or the like.

A "lower alkynyl group" is a linear or branched alkynyl group of 2 to 6 carbons, such as an ethynyl group, a propynyl group, a butynyl group or the like.

A "lower alkoxy group" is a linear or branched alkoxy group of 1 to 6 carbons, such as a methoxy group, an ethoxy group, a n-propoxy group, an i-propoxy group, a n-butoxy group, a s-butoxy group, a t-butoxy group, a pentoxy group, a hexoxy group or the like.

An "acyl group" is a carbonyl group substituted with a hydrogen atom or with an alkyl group with an optional substituent, an aryl group with an optional substituent, an alkoxy group with an optional substituent, an amino group with an optional substituent or the like, for example, an alkylcarbonyl group such as an acetyl group, a propionyl group, a pivaloyl group, a cyclohexanecarbonyl group or the like, or an arylcarbonyl group such as a benzoyl group, a naphthoyl group, a toluoyl group or the like.

An "aryl group" is a monovalent group which is an aromatic hydrocarbon minus one hydrogen atom, such as a phenyl group, a tolyl group, a xylyl group, a biphenyl group, a naphthyl group, an anthryl group, a phenanthryl group or the like.

A "lower alkylene group" is a linear or branched alkylene group of 1 to 6 carbons, such as a methylene group, an ethylene group, a propylene group, a butylene group, a pentylene group, a hexylene group or the like.

A "cycloalkyl group" is a cyclic saturated hydrocarbon group of 3 to 8 carbons, such as a cyclopropyl group, a cyclobutyl group, a cyclopentyl group, a cyclohexyl group or a cycloheptyl group. And, substituted cycloalkyl groups include menthyl group, adamantyl group and the like.

A "heterocyclic group" is an aromatic heterocyclic group with at least one hetero atom, such as a pyridyl group, a furyl group, a thienyl group, an imidazolyl group, a pyrazinyl group, a pyrimidyl group or the like.

The aforementioned lower alkyl group, lower alkenyl group, alkynyl group, lower alkoxy group, acyl group, aryl group, cycloalkyl group and heterocyclic group may, if necessary, be substituted with one or more substituents. As examples of such substituents there may be a halogen atom, a lower alkyl group, a cycloalkyl group, an aryl group, a hydroxyl group, a lower alkoxy group which alkoxy group may be substituted with a halogen atom, an aryloxy group, a lower alkylthio group, a heterocyclic group, a formyl group which formyl group may be protected as an acetal, a lower alkylcarbonyl group, an arylcarbonyl group, a carboxyl group, a lower alkoxycarbonyl group, an amino group which amino group may have a lower alkyl group, etc., an imino group, a thioacetal group, a nitro group, a nitrile group, a trifluoromethyl group and the like.

The compounds serving as the active ingredients in the chondrogenesis promoters and cartilage repair agents of the invention (indolin-2-one derivatives represented by the above general formula (I)) will now be explained in greater detail.

$R^1$ represents a halogen atom, a lower alkyl group, a lower alkoxy group, a hydroxyl group, a nitro group, a trifluoromethyl group, a lower alkylthio group, an acyl group, a carboxyl group, a mercapto group or an amino group with an optional substituent, and among these, $R^1$ is preferably a halogen atom, a lower alkyl group, a lower alkoxy group or a nitro group.

The subscript "n" represents an integer of 0 to 4. It is preferably 0 or 1, and most preferably 0.

$R^2$ represents a hydrogen atom, a lower alkyl group with an optional substituent, a lower alkenyl group with an optional substituent, a lower alkynyl group with an optional substituent, a lower alkoxy group with an optional substituent, an acyl group with an optional substituent, an aryl group with an optional substituent or a heterocyclic group with an optional substituent.

$R^2$ is preferably a hydrogen atom, a lower alkyl group with an optional substituent, a lower alkenyl group with an optional substituent or an aryl group with an optional substituent, and from the viewpoint of activity as a chondrogenesis promoter or cartilage repair agent, it is even more preferably a lower alkyl group with an optional substituent which is optionally substituted with a halogen atom.

Among these, $R^2$ is yet more preferably a lower alkyl group substituted at the same carbon with two lower alkoxy groups which are optionally substituted with 1–5 halogen atoms or the group —O—Z—O— wherein Z represents a lower alkylene group optionally substituted with 1–10 halogen atoms, and still more preferably, a group represented by general formula (II):

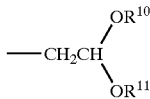

(II)

wherein $R^{10}$ and $R^{11}$ may be the same or different, and each represents a lower alkyl group optionally substituted with 1–5 halogen atoms, preferably either or both being lower alkyl groups with 1–5 halogen atoms, or general formula (III):

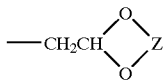

(III)

wherein Z represents a lower alkylene group optionally substituted with 1–10 halogen atoms.

$R^2$ is more preferably a 2,2-diethoxyethyl group, a 2,2-dimethoxyethyl group, a 2,2-diisopropoxyethyl group, a 2,2-bis(2-fluoroethoxy)ethyl group or a 2,2-bis(2-chloroethoxy)ethyl group, among which a 2,2-diethoxyethyl group and a 2,2-bis(2-fluoroethoxy)ethyl group are most preferred, and a 2,2-diethoxyethyl group is particularly preferred.

$R^3$ represents a lower alkyl group with an optional substituent, a cycloalkyl group with an optional substituent, an aryl group with an optional substituent or a heterocyclic group with an optional substituent. $R^3$ is preferably a lower alkyl group with an optional substituent, a cycloalkyl group with an optional substituent or an aryl group with an optional substituent, among which an aryl group with an optional substituent is particularly preferred. Preferred as the substituent is a lower alkyl group (preferably a methyl group and an ethyl group, and especially a methyl group) and an amino group optionally having a lower alkyl group, and a 4-methylphenyl group is especially preferred for $R^3$.

$R^4$ represents a hydrogen atom, a lower alkyl group with an optional substituent, an aryl group with an optional substituent, a heterocyclic group with an optional substituent, —$OR^5$, —$SR^5$ or —$NR^6R^7$. Here, $R^5$, $R^6$ and $R^7$ may be the same or different and each represents a hydrogen atom, a lower alkyl group with an optional substituent, a cycloalkyl group with an optional substituent, an aryl group with an optional substituent, a heterocyclic group with an optional substituent, a lower alkoxy group or an amino group with an optional substituent, and $R^6$ and $R^7$ may together form a group represented by —(CH$_2$)$_m$— or —(CH$_2$)$_l$NR$^8$(CH$_2$)$_k$— wherein k, l and m each represent an integer of 1–8 and $R^8$ represents a hydrogen atom or a lower alkyl group.

$R^4$ is preferably a lower alkyl group with an optional substituent, an aryl group with an optional substituent, a heterocyclic group with an optional substituent or a group represented by —$OR^5$ or —$NR^6R^7$ wherein $R^5$, $R^6$ and $R^7$ are as previously defined, and it is more preferably the group —$NR^6R^7$ wherein $R^6$ and $R^7$ may be the same or different and each represents a hydrogen atom or an aryl group with an optional substituent.

Among these, $R^4$ is preferably a group represented by —$NR^6R^7$ wherein $R^6$ and $R^7$ may be the same or different and each represents a hydrogen atom or an aryl group which aryl group has a lower alkyl group or amino group which amino group optionally has a lower alkyl group, and it is most preferably a group represented by —$NHR^7$ wherein $R^7$ is a 4-methylphenyl group, a 4-ethylphenyl group or a 4-(N,N-dimethylamino)phenyl group.

X and Y may be the same or different and represent —CH$_2$—, —NH— or —O—, among which X is preferably —CH$_2$—, —NH— or —O— and Y is preferably —CH$_2$— or —NH—. From the viewpoint of activity as a chondrogenesis promoter or cartilage repair agent, X and Y may be the same or different and are preferably —CH$_2$— or —NH—, and most preferably, X is —NH— and Y is —CH$_2$—.

The indolin-2-one derivatives of the invention may be used in the form of pharmaceutically acceptable salts. As examples of such salts there may be mentioned inorganic salts such as hydrochloric acid salts, hydrobromic acid salts, hydroiodic acid salts, sulfuric acid salts and phosphoric acid salts; organic acid salts such as succinic acid salts, malonic acid salts, acetic acid salts, maleic acid salts, fumaric acid salts, citric acid salts, benzoic acid salts and salicylic acid salts; and metal salts such as sodium salts, potassium salts and magnesium salts.

The indolin-2-one derivatives of the invention may also be optically active forms. When in optically active forms, the absolute configuration at the 3 position is preferably the R configuration.

As examples of specific compounds which are indolin-2-one derivatives according to the invention there may be mentioned the compounds mentioned in the examples of WO94/19322, as well as the compounds mentioned in the examples of Japanese Patent Application Laid-Open No. 7-48349, namely, Compound Nos. 1–201 listed in the following tables (Tables 1–9).

In Tables 1–9, $R^1$—$R^4$, X, Y and n have the same definitions as for general formula (I) above.

TABLE 1

| COMPOUND NO. | $(R^1)n$ | $R^2$ | X | $R^3$ | Y | $R^4$ |
|---|---|---|---|---|---|---|
| 1 | — | —CH$_2$—C$_6$H$_5$ | NH | —C$_6$H$_4$—CH$_3$ | NH | —NH—C$_6$H$_4$—CH$_3$ |
| 2 | 5-NO$_2$ | H | " | " | " | " |
| 3 | — | —CH$_2$CH=CH$_2$ | " | " | " | " |
| 4 | — | —C$_6$H$_5$ | " | " | " | " |
| 5 | — | —CH$_2$CH(OCH$_3$)$_2$ | " | " | " | " |
| 6 | — | —CH$_2$CH(OC$_3$H$_7$-n)$_2$ | " | " | " | " |
| 7 | — | —CH$_2$CH(OCH$_3$)(OC$_2$H$_5$) | " | " | " | " |
| 8 | — | H | " | " | " | " |
| 9 | — | H | " | —C$_6$H$_5$ | " | —NH—C$_6$H$_5$ |
| 10 | — | —CH$_2$CH(OC$_2$H$_5$)$_2$ | " | —C$_6$H$_4$—CH$_3$ | " | —NH—C$_6$H$_4$—CH$_3$ |
| 11 | — | " | " | —C$_6$H$_4$—OCH$_3$ | " | —NH—C$_6$H$_4$—OCH$_3$ |
| 12 | — | " | " | —C$_6$H$_4$—COOCH$_3$ | " | —NH—C$_6$H$_4$—COOCH$_3$ |
| 13 | — | " | " | —C$_6$H$_4$—CN | " | —NH—C$_6$H$_4$—CN |
| 14 | — | " | " | —C$_6$H$_4$—F | " | —NH—C$_6$H$_4$—F |
| 15 | — | " | " | —C$_6$H$_4$—F (meta) | " | —NH—C$_6$H$_4$—F (meta) |

TABLE 1-continued

| COMPOUND NO. | (R¹)n | R² | X | R³ | Y | R⁴ |
|---|---|---|---|---|---|---|
| 16 | — | " | " | 4-nitrophenyl | " | —NH—(4-nitrophenyl) |
| 17 | — | " | " | 4-(CF₃)phenyl | " | —NH—(4-(CF₃)phenyl) |
| 18 | — | " | " | 2-fluorophenyl | " | —NH—(2-fluorophenyl) |
| 19 | — | " | " | 2-cyanophenyl | " | —NH—(2-cyanophenyl) |
| 20 | — | " | " | 4-bromophenyl | " | —NH—(4-bromophenyl) |

TABLE 2

| COMPOUND NO. | (R¹)n | R² | X | R³ | Y | R⁴ |
|---|---|---|---|---|---|---|
| 21 | — | —CH₂CH(OC₂H₅)₂ | NH | 3-bromophenyl | NH | —NH—(3-bromophenyl) |
| 22 | — | H | CH₂ | 4-methylphenyl | CH₂ | —NH—(4-methylphenyl) |
| 23 | — | —CH₂—phenyl | " | " | " | " |
| 24 | — | CH₃ | " | " | " | " |
| 25 | — | —CH₂CO—phenyl | " | " | " | " |
| 26 | — | —CH₂-(2-pyridyl) | " | " | " | " |
| 27 | — | —CH₂—phenyl | O | " | " | " |
| 53a | — | —CH₂COOC₂H₅ | NH | " | " | OC₂H₅ |
| 53b | — | H | " | " | " | " |

TABLE 2-continued

| COMPOUND NO. | (R¹)n | R² | X | R³ | Y | R⁴ |
|---|---|---|---|---|---|---|
| 54a | — | —CH₂CO—C₆H₅ (phenyl) | " | " | " | 4-methylphenyl |
| 54b | — | H | " | " | " | " |
| 55 | — | " | " | " | " | OH |
| 56 | — | —CH₂COOH | " | " | " | " |
| 57 | — | H | " | " | " | —NH—C₆H₄—CH₃ (4-methyl) |
| 58 | — | " | " | " | " | 4-methylpiperazin-1-yl |
| 59 | — | " | " | " | " | piperidin-1-yl |
| 60 | — | " | CH₂ | " | NH | —CH₂—C₆H₄—CH₃ (4-methyl) |
| 61 | — | —CH₂—C₆H₅ | " | " | " | CH₃ |
| 62 | — | " | " | " | " | —NH—C₆H₄—CH₃ (4-methyl) |
| 63 | — | —CH₂CO—C₆H₅ | NH | " | CH₂ | ditto |

TABLE 3

| COMPOUND NO. | (R¹)n | R² | X | R³ | Y | R⁴ |
|---|---|---|---|---|---|---|
| 64 | — | —CH₂COOC₂H₅ | NH | 4-methylphenyl | CH₂ | —NH—C₆H₄—CH₃ (4-methyl) |
| 65 | — | —CH₂-(pyridin-2-yl) | " | " | " | " |
| 66 | — | —CH₂CH₂—C₆H₅ | " | " | " | " |
| 67 | — | CH₃ | " | " | " | " |
| 68 | — | —CH₂-(pyridin-4-yl) | " | " | " | " |
| 69 | — | —CH₂OCH₃ | " | " | " | " |
| 70 | — | —CH₂CH(C₃H₇-n)₂ | " | " | " | " |

TABLE 3-continued
| COMPOUND NO. | (R¹)n | R² | X | R³ | Y | R⁴ |
|---|---|---|---|---|---|---|
| 71 | — | —CH₂CH(OC₂H₅)₂ | " | " | " | " |
| 72 | 7-CH₃ | H | " | " | " | " |
| 73 | — | 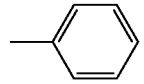 | " | " | " | " |
| 74 | 5-CH₃ | —CH₂CH(OC₂H₅)₂ | " | " | " | " |
| 75 | 5-F | " | " | " | " | " |
| 76 | 5-OCH₃ | " | " | " | " | " |
| 77 | 5-Br | " | " | " | " | " |
| 78 | — | " | " | 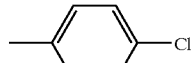 | " | " |
| 79 | — | " | " | 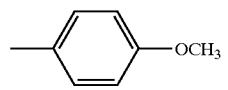 | " | " |
| 80 | — | " | " | 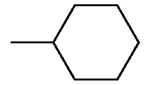 | " | " |
| 81 | — | " | " | 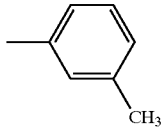 | " | " |
| 82 | — | " | " | 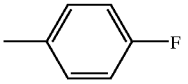 | " | " |
| 83 | — | " | " | 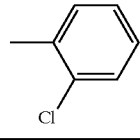 | " | " |
TABLE 4
| COMPOUND NO. | (R¹)n | R² | X | R³ | Y | R⁴ |
|---|---|---|---|---|---|---|
| 84 | — | —CH₂CH(OC₂H₅)₂ | NH | 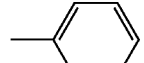 | CH₂ | 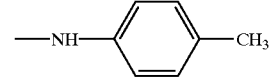 |
| 85 | — | " | " | 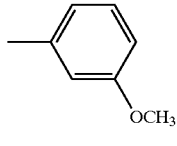 | " | " |
| 86 | — | " | " | C₂H₅ | " | " |
| 87 | — | " | " | 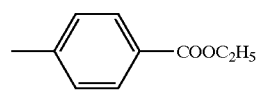 | " | " |

TABLE 4-continued
| COMPOUND NO. | $(R^1)n$ | $R^2$ | X | $R^3$ | Y | $R^4$ |
|---|---|---|---|---|---|---|
| 88 | — | " | " | 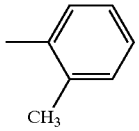 | " | " |
| 89 | — | " | " | 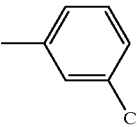 | " | " |
| 90 | — | " | " | 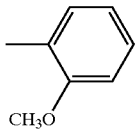 | " | " |
| 91 | — | " | " | 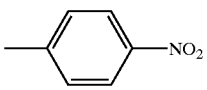 | " | " |
| 92 | — | " | " | 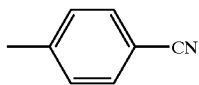 | " | " |
| 93 | — | " | " | 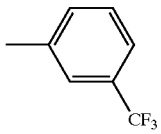 | " | " |
| 94 | — | " | " | 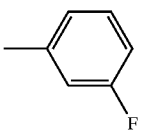 | " | " |
| 95 | — | " | " | 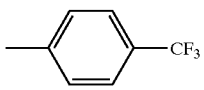 | " | " |
| 96 | — | —CH$_2$CH(OC$_3$H$_7$-n)$_2$ | " | 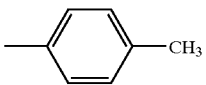 | " | " |
| 97 | — | —CH$_2$CHO | " | " | " | " |
| 98 | — | 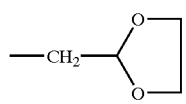 | " | " | " | " |
| 99 | — | 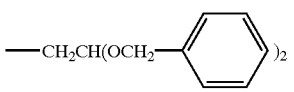 | " | " | " | " |
| 100 | — | —CH$_2$CH(OCH$_3$)$_2$ | " | " | " | " |

TABLE 4-continued

| COMPOUND NO. | (R¹)n | R² | X | R³ | Y | R⁴ |
|---|---|---|---|---|---|---|
| 101 | — | -CH₂-[2,2-disubstituted-1,3-dioxane with 4,6-di-CH₃] | " | " | " | " |
| 102 | — | —CH₂CH₂NHCH₃·HCl | " | " | " | " |
| 103 | — | —CH₂CH₂—N(piperidine) | " | " | " | " |

TABLE 5

| COMPOUND NO. | (R¹)n | R² | X | R³ | Y | R⁴ |
|---|---|---|---|---|---|---|
| 104 | — | —CH₂CH₂N(CH₃)₂ | NH | —C₆H₄—CH₃ (para) | CH₂ | —NH—C₆H₄—CH₃ |
| 105 | — | —CH₂CH(SCH₃)₂ | " | " | " | " |
| 106 | — | —CH₂CH(SC₂H₅)₂ | " | " | " | " |
| 107 | — | —CH₂CH(OC₂H₅)₂ | " | " | " | OC₂H₅ |
| 108 | — | " | " | " | " | OH |
| 109 | — | " | " | " | " | —N(CH₃)—C₆H₅ |
| 110 | — | " | " | " | " | —NH—C₆H₄—COOCH₃ |
| 111 | — | " | " | " | " | —NH—C₆H₄—CH₃ (meta) |
| 112 | — | " | " | " | " | —NH—C₆H₄—CH₃ (ortho) |
| 113 | — | " | " | " | " | —NHC₃H₇-n |
| 114 | — | " | " | " | " | —NH—C₆H₄—Cl |
| 115 | — | " | " | " | " | —NH—C₆H₄—OCH₃ |
| 116 | — | " | " | " | " | —NH(CH₂)₃COOC₂H₅ |
| 117 | — | " | " | " | " | —NHOCH₃ |

TABLE 5-continued

| COMPOUND NO. | (R¹)n | R² | X | R³ | Y | R⁴ |
|---|---|---|---|---|---|---|
| 118 | — | " | " | " | " | —NH—C₆H₄—CH₂COOCH₃ |
| 119 | — | " | " | " | " | —NHCH₂CH(OC₂H₅)₂ |
| 120 | — | " | " | " | " | —NH—C₆H₄—C₆H₁₃ |
| 121 | — | " | " | " | " | —NH—C₆H₄—NO₂ |
| 122 | — | " | " | " | " | —NH—C₆H₃(CH₃)(CH₃) |
| 123 | — | " | " | " | " | —NH—C₆H₄—Cl (3-Cl) |

TABLE 6

| COMPOUND NO. | (R¹)n | R² | X | R³ | Y | R⁴ |
|---|---|---|---|---|---|---|
| 124 | — | —CH₂CH(OC₂H₅)₂ | NH | —C₆H₄—CH₃ | CH₂ | —NH—C₆H₄—F |
| 125 | — | " | " | " | " | —NH—C₆H₄—NH₂ |
| 126 | — | " | " | " | " | —NHCH₂—C₆H₅ |
| 127 | — | " | " | " | " | —NH—C₆H₄—OH |
| 128 | — | " | " | " | " | —NH—C₆H₄—CF₃ |
| 129 | — | " | " | " | " | —NH—C₆H₄—OCH₃ (3-OCH₃) |

TABLE 6-continued

| COMPOUND NO. | (R¹)n | R² | X | R³ | Y | R⁴ |
|---|---|---|---|---|---|---|
| 130 | — | " | " | " | " | —NH—C₆H₄—N(CH₃)₂ |
| 131 | — | " | " | " | " | —NH—C₆H₄—N(CH₃)(COCF₃) |
| 132 | — | " | " | " | " | —NH-(pyrimidin-2-yl) |
| 133 | — | " | " | " | " | —NH—C₆H₅ |
| 134 | — | " | " | " | " | —NH—C₆H₄—N(C₂H₅)₂ |
| 135 | — | " | " | " | " | —NH—C₆H₄—NHCOCF₃ |
| 136 | — | " | " | " | " | —NH-(1-COCF₃-indolin-5-yl) |
| 137 | — | " | " | " | " | —NH-(1H-indol-5-yl) |
| 138 | — | " | " | " | " | —NH-(5-methylpyridin-2-yl) |
| 139 | — | " | " | " | " | —NH-(2-chlorophenyl) |
| 140 | — | " | " | " | " | —NH-(pyridin-4-yl) |
| 141 | — | " | " | " | " | —NH-(3-methoxyphenyl) |
| 142 | — | " | " | " | " | —NH-(2-hydroxy-5-methylphenyl) |

TABLE 6-continued

| COMPOUND NO. | (R¹)n | R² | X | R³ | Y | R⁴ |
|---|---|---|---|---|---|---|
| 143 | — | " | " | " | " | —NH-(5-pyridyl-2-OCH₃) |

TABLE 7

| COMPOUND NO. | (R¹)n | R² | X | R³ | Y | R⁴ |
|---|---|---|---|---|---|---|
| 144 | — | —CH₂CH(OC₂H₅)₂ | NH | 4-CH₃-phenyl | CH₂ | —NH-(2-pyridyl) |
| 145 | — | " | " | " | " | —NH-(3-pyridyl) |
| 146 | — | " | " | 3-OCH₃-phenyl | " | —OC₂H₅ |
| 147 | — | " | " | " | " | —OH |
| 148 | — | " | " | " | " | —NH-(4-OCH₃-phenyl) |
| 149 | — | " | " | " | " | —NH-(4-Cl-phenyl) |
| 150 | — | " | " | " | " | —NH-(2-CH₃-phenyl) |
| 151 | — | " | " | " | " | —NH-(3-OCH₃-phenyl) |
| 152 | — | " | " | " | " | —NH-(3-CH₃-phenyl) |
| 153 | — | " | " | " | " | —NH-(2-OCH₃-phenyl) |

TABLE 7-continued

| COMPOUND NO. | (R¹)n | R² | X | R³ | Y | R⁴ |
|---|---|---|---|---|---|---|
| 154 | — | " | " | " | " | 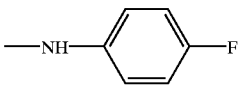—NH—⟨C₆H₄⟩—F |
| 155 | — | " | " | " | " | —NHC₃H₇-n |
| 156 | — | " | " | " | " | —NH—⟨C₆H₄⟩—N(CH₃)₂ |
| 157 | — | " | " | " | " | 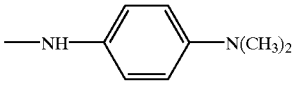—NH—⟨C₆H₄⟩—COOCH₃ |
| 158 | — | " | " | " | " | 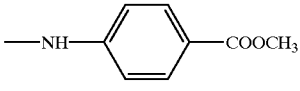—NH—⟨pyridine⟩—CH₃ |
| 159 | — | —CH₂CHO | " | " | " | 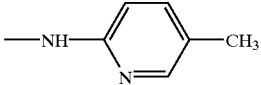—NH—⟨C₆H₄⟩—CH₃ |
| 160 | — | —CH₂CH₂N(CH₃)₂ | " | " | " | " |
| 161 | — | —CH₂CH(OC₂H₅)₂ | " | 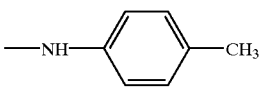—⟨C₆H₄⟩—CH₃ | " | 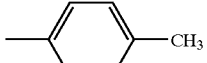—NH—⟨C₆H₄⟩—NHCH₃ |
| 162 | — | " | " | " | " | 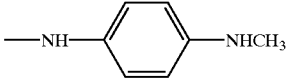—NH—⟨indoline⟩ |
| 163 | — | " | " | " | " | 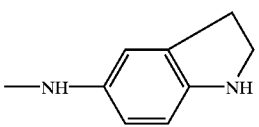—NH—⟨C₆H₄⟩—COOH |

TABLE 8

| COMPOUND NO. | (R¹)n | R² | X | R³ | Y | R⁴ |
|---|---|---|---|---|---|---|
| 164 | — | —CH₂CH(OC₂H₅)₂ | NH | 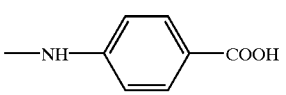—⟨C₆H₄⟩—CH₃ | CH₂ | 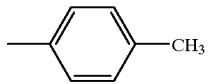—NH—⟨C₆H₄⟩—CH₂COOH |
| 165 | — | " | CH₂ | " | NH | —NH—⟨C₆H₄⟩—COOH |
| 166 | — | " | " | " | " | 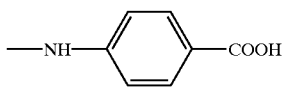—NH—⟨C₆H₄⟩—NH₂ |
| 167 | — | " | " | " | " | 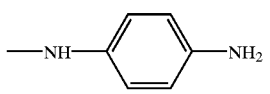—NH—⟨C₆H₄⟩—N(CH₃)₂ |

TABLE 8-continued

| COMPOUND NO. | (R¹)n | R² | X | R³ | Y | R⁴ |
|---|---|---|---|---|---|---|
| 168 | — | " | NH | 4-Cl-C₆H₄- | CH₂ | —NH-C₆H₄-4-Cl |
| 169 | — | " | " | 4-OCH₃-C₆H₄- | " | " |
| 170 | — | " | " | 4-F-C₆H₄- | " | —NH-C₆H₄-4-F |
| 171 | — | " | " | 4-CH₃-C₆H₄- | " | —O-(L-Menthyl) |
| 172 | — | " | " | " | " | " |
| 173 | — | " | " | " | " | —O-(D-Menthyl) |
| 174 | — | " | " | 4-CH₃-C₆H₄- | " | —NH-C₆H₄-4-CH₃ |
| 175 | — | " | " | " | " | " |
| 176 | — | " | " | " | " | —NH-C₆H₄-4-I |
| 177 | — | " | " | " | " | —OCH₂CH₂Br |
| 178 | — | " | " | " | " | —OCH₂CH₂I |
| 179 | — | " | " | " | " | —NH-(5-CH₃-pyridin-2-yl) |
| 180 | — | " | " | " | " | —NH-C₆H₄-4-N(CH₃)₂ |
| 181 | — | " | " | " | " | —NH-(6-OCH₃-pyridin-3-yl) |
| 182 | — | " | " | " | " | —NH-(5-CH₃-pyridin-2-yl) |
| 183 | — | " | " | " | " | —NH-C₆H₄-4-N(CH₃)₂ |

TABLE 9

| COMPOUND NO. | (R¹)n | R² | X | R³ | Y | R⁴ |
|---|---|---|---|---|---|---|
| 184 | — | —CH₂CH(OC₂H₅)₂ | NH | ![4-methylphenyl] | CH₂ | —NH-(5-methoxypyridin-3-yl) |
| 185 | — | " | " | ![3-methoxyphenyl] | " | —O-(L-Menthyl) |
| 186 | — | " | " | " | " | " |
| 187 | — | " | " | " | " | —O-(D-Menthyl) |
| 188 | — | " | " | " | " | —NH-(4-methylphenyl) |
| 189 | — | " | " | " | " | " |
| 190 | — | " | " | " | " | —NH-(5-methylpyridin-2-yl) |
| 191 | — | " | " | " | " | —NH-(4-N(CH₃)₂-phenyl) |
| 192 | — | " | " | " | " | —NH-(5-methylpyridin-2-yl) |
| 193 | — | " | " | " | " | —NH-(4-N(CH₃)₂-phenyl) |
| 194 | — | " | " | " | " | " |
| 196 | — | " | " | ![4-methylphenyl] | " | —OCH₂-(4-bromophenyl) |
| 197 | — | " | " | " | " | —O-(S)-sec-butyl |
| 198 | — | —CH₂CHO | " | " | " | —NH-(4-methylphenyl) |
| 199 | — | " | " | " | " | —OH |
| 200 | — | " | " | " | " | —O-(L-Menthyl) |
| 201 | — | —CH₂CH=NOH | " | " | " | —NH-(4-methylphenyl) |

As examples of specific compounds more suitable as chondrogenesis promoters and cartilage repair agents according to the invention there may be mentioned the following compounds.

(Compound A)
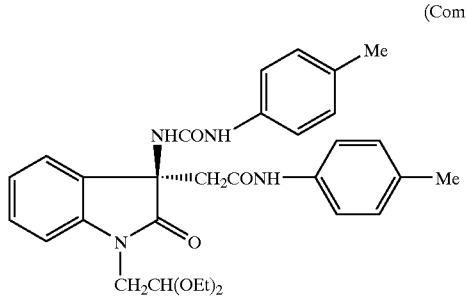

(Compound B)
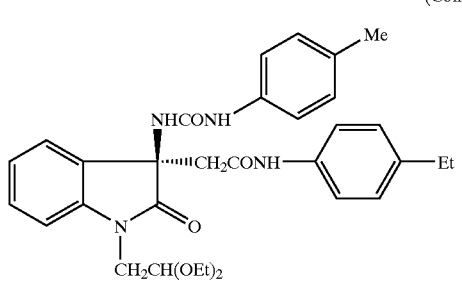

(Compound C)
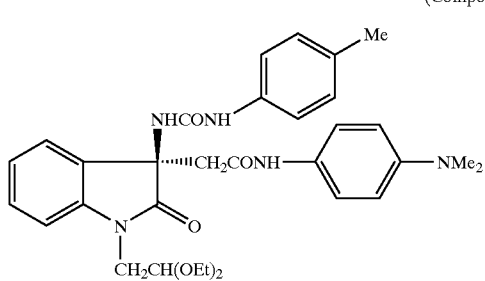

(Compound D)
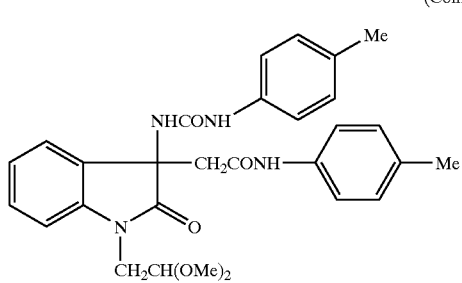

(Compound E)
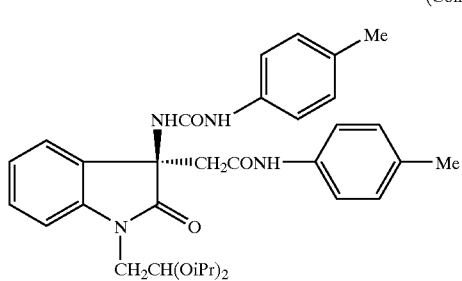

(Compound F)
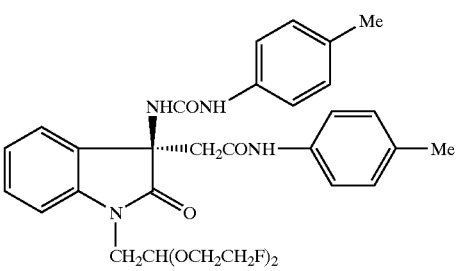

(Compound G)
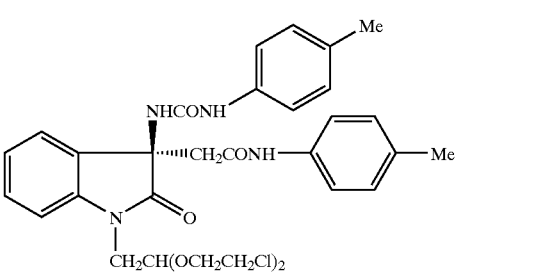

As examples of biometabolites of compound A there may be mentioned the following compounds H and I.

(Compound H)
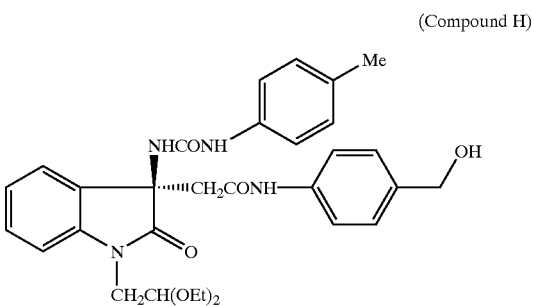

(Compound I)
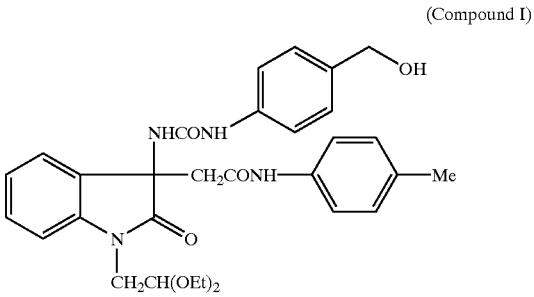

The compounds listed in Tables 1 to 9 may be synthesized by the process described in Japanese Patent Application Laid-Open No. 7-48349. Of the compounds A to G mentioned above, compounds A to D may be synthesized by the process described in Japanese Patent Application Laid-Open No. 7-48349.

Compounds E, F and G may be synthesized, for example, by Reaction Path A shown below (corresponding to "Reaction Path 6" in Japanese Patent Application Laid-Open No. 7-48349), using as the starting material the aldehyde intermediate mentioned in the examples of the present application, synthesized according to the process described in Japanese Patent Application Laid-Open No. 7-48349.

Reaction Path A

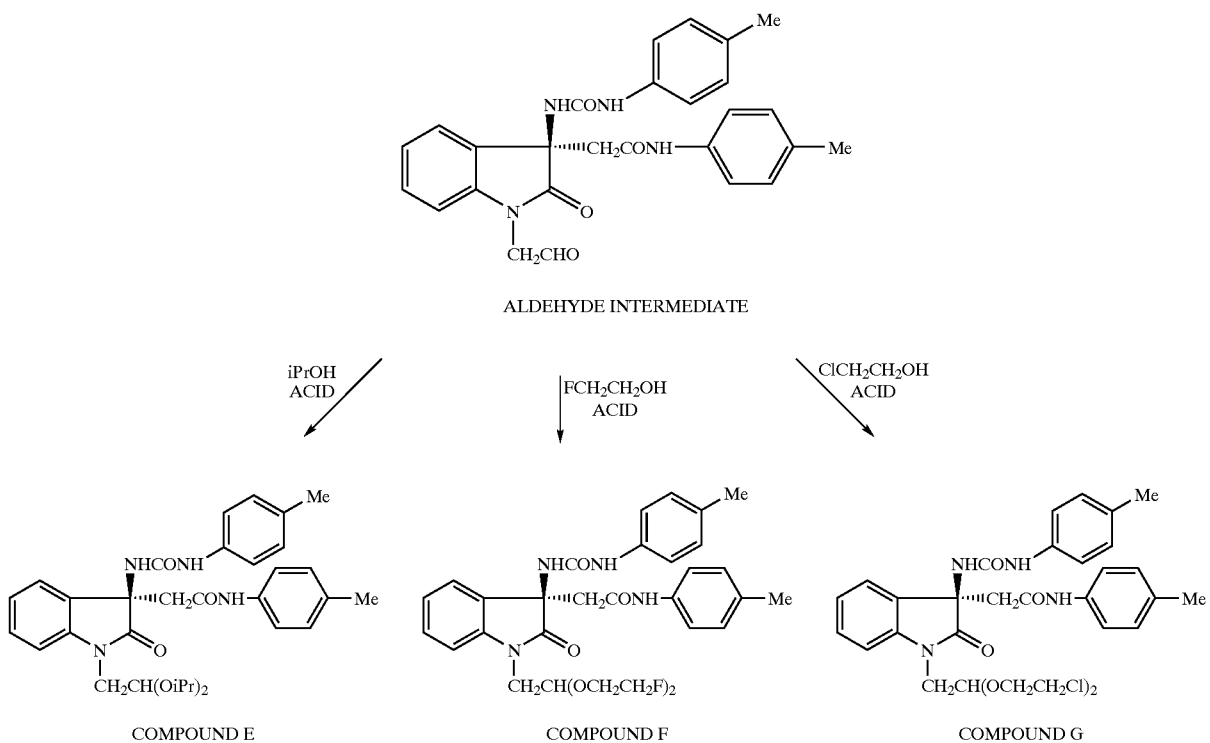

ALDEHYDE INTERMEDIATE

Compound H mentioned above may be synthesized according to "Reaction Path 7" in Japanese Patent Application Laid-Open No. 7-48349. Compound I may be obtained by the following process, either in a racemic form or optically active form.

Specifically, a racemic form of compound I may be synthesized, for example, according to the following Reaction Path B (corresponding to "Reaction Path 5" in Japanese Patent Application Laid-Open No. 7-48349), using an isocyanate having a hydroxyl group protected with a suitable protecting group (for example, a substituted silyl group such as a triethylsilyl group, a t-butyldimethylsilyl group or the like).

An optically active form of compound I may be synthesized, for example, according to the following Reaction Path B (corresponding to "Reaction Path 7" in Japanese Patent Application Laid-Open No. 7-48349), using an isocyanate having a hydroxyl group protected with a suitable protecting group (for example, a substituted silyl group such as a triethylsilyl group, a t-butyldimethylsilyl group or the like), or by optically separating a stereoisomeric mixture of compound I by a method well known to those skilled in the art (for example, a method using an optically active column).

Identification, structure determination and purity determination of the obtained compound may be accomplished by ordinary methods (spectroscopic methods such as NMR, IR, etc. and high performance liquid chromatography or the like).

Reaction Path B

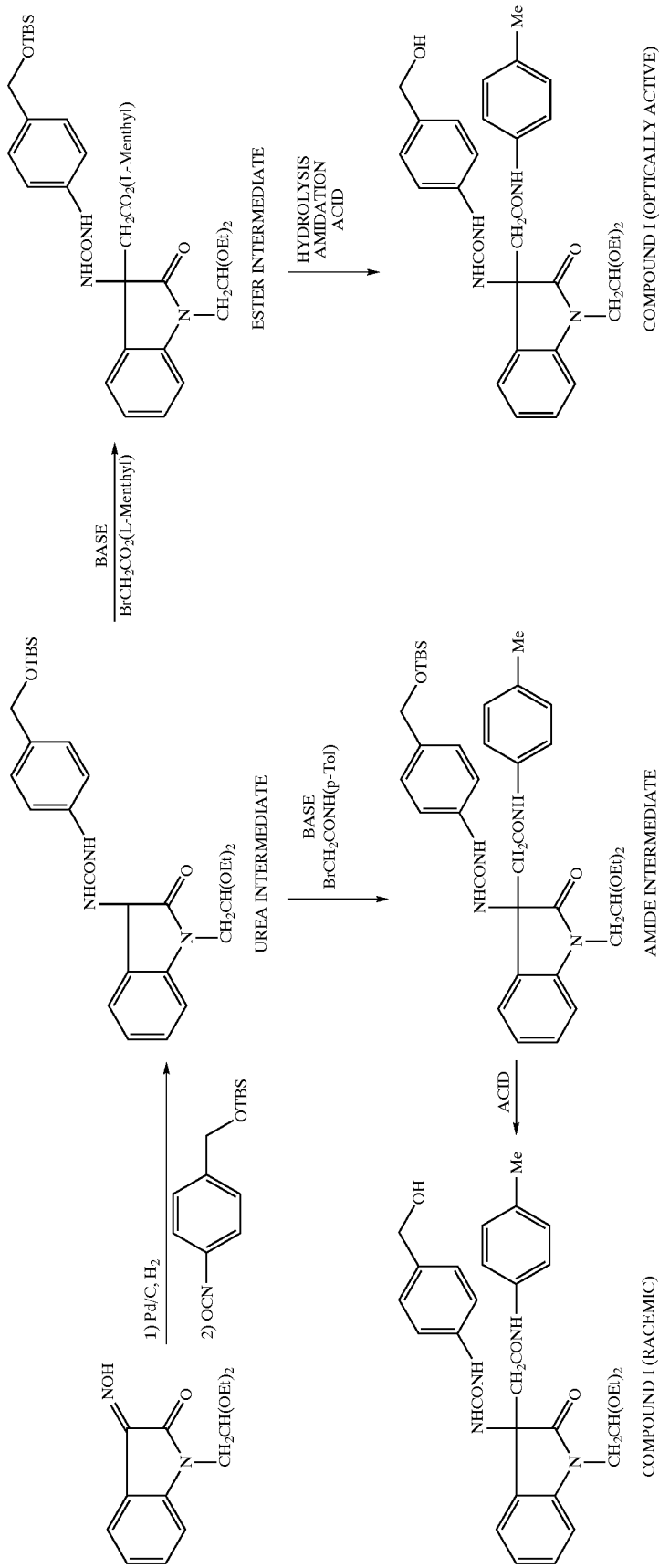

A chondrogenesis promoter according to the invention may be applied for a variety of uses without any particular restrictions, so long as the chondrogenesis promoting effect of the agent can be effectively utilized; it is particularly useful for treatment of chondropathy accompanying cartilage dysfunction due to degeneration or destruction of cartilage, treatment of damage or ablation of cartilage due to injury or surgery, or treatment of congenital cartilage hypoplasia or malformation. Examples of such chondropathic conditions include osteoarthritis, chronic rheumatoid arthritis, dissecting osteochondrosis, injury-induced articular cartilage damage, herniated intervertebral disk, and the like. Examples of congenital cartilage hypoplasia or malformation include anotia and microtia.

An agent containing a compound according to the invention may be administered either orally or parenterally, but parenteral administration is preferred from the standpoint of avoiding unnecessary promotion of chondrogenesis outside of the site of administration, and from the standpoint of the effect. The agent may be formulated in a manner suitable for the method of administration.

A pharmaceutical composition comprising a compound of the invention as an active ingredient may be formulated using an ordinary formulation technique. The pharmaceutical composition may be used in various forms depending on the purpose of use, such as in the form of capsules, granules, cream, powder, syrup, tablets, injection or ointment, and either in solid or liquid form. The carrier or excipient used for the formulation may be a solid or liquid substance. As examples there may be mentioned lactose, magnesium stearate, starch, talc, gelatin, agar, pectin, gum Arabic, olive oil, sesame oil, ethylene glycol and the like, as well as any other commonly used substance.

The content of the compound of the invention in the formulation will differ depending on the form of preparation, but usually a concentration of 0.00001–80 wt % is preferred. A pharmaceutical composition of a compound of the invention may administered in various dosages depending on the type of warm-blooded animal, such as a human, the severity of symptoms and the clinical diagnosis; in most cases, however, the daily oral dosage will be 0.01–2 g/kg and the daily parenteral dosage will be 0.0000001–0.01 g/kg. This dosage may be given at once or spread over several times every 1 to 7 days, with appropriate adjustment depending on the severity of symptoms and the clinical diagnosis.

As shown in the examples provided below, agents according to the invention were shown to have chondrogenesis promoting effects when administered orally or parenterally to rats. This indicates the usefulness of these agents as therapeutic agents for cartilage disease.

Also, the chondrogenesis promoting effects exhibited by compounds represented by general formula (I) on tracheal cartilage, interspinal disks, auricular cartilage and sternal cartilage indicate that the compounds represented by general formula (I) can constitute useful therapies as repair agents for diseases characterized by cartilage defect and degeneration or destruction of cartilage.

Moreover, treatment of undifferentiated mesenchymal cells (CL-1) or chondrocytes with chondrogenesis promoters represented by general formula (I) can yield chondrocytes (or more abundant chondrocytes if it is chondrocytes that are treated), as well as the extracellular matrix or cartilage-like tissue. The chondrogenesis promoters described in the present application may be used for analysis of extracellular matrix metabolism of chondrocytes and the mechanism of differentiation into chondrocytes (biological properties), analysis of the components constituting the extracellular matrix (chemical properties), and analysis of properties such as viscoelasticity (physical properties).

Furthermore, the indolin-2-one derivatives represented by general formula (I) of the invention that exhibit chondrogenesis promoting effects may, in some cases, promote calcified chondrogenesis by the same chondrogenesis promoting effect, thus eliciting, in such cases, a bone fracture cure promoting effect via eventual endochondral ossification by the compounds. That is, these compounds are also expected to be useful as bone fracture repair promoters.

The present invention will now be explained in more concrete detail by way of the following examples.

EXAMPLES

Synthesis Example 1

Compounds A, C and D were synthesized by the following method.

Compound A

Synthesis was carried out by the method described in "Example 174(2)" of Japanese Patent Application Laid-Open No. 7-48349. A racemic form of the compound was synthesized by the method described in "Example 71" of the patent publication.

Compound C

Synthesis was carried out by the method described in "Example 180" of Japanese Patent Application Laid-Open No. 7-48349.

Compound D

Synthesis was carried out by the method described in "Example 100" of Japanese Patent Application Laid-Open No. 7-48349.

Synthesis Example 2

Compounds B, E, F and G were synthesized by the following method.

Compound B (3R)-1-(2,2-diethoxyethyl)-3-(4-ethylphenyl)aminocarbonylmethyl-3-(N'-(4-methylphenyl)ureido)indolin-2-one (+)-1-(2,2-diethoxyethyl)-3-hydroxycarbonylmethyl-3-(N'-(4-methylphenyl)ureido)indolin-2-one (compound described in "Example 174(1)" of Japanese Patent Application Laid-Open No. 7-48349, 182 mg) was dissolved in dichlormethane (10 mL), and then 1-ethyl-3-(3-dimethylaminopropyl)-carbodiimide hydrochloride (96 mg) and para-ethylaniline (61 mg) were added. The resulting mixture was stirred at 15–30° C. for 15 hours.

The reaction mixture was washed with 1N diluted hydrochloric acid and then with saturated bicarbonate water, and after drying on anhydrous sodium sulfate (15–30° C.), the solvent was removed under reduced pressure for concentration. The residue was purified by silica gel column chromatography (hexane/ethyl acetate=3/1) to obtain 145 mg of the title compound as a white powder (yield: 65%).

NMR (CDCl$_3$, 270 MHz)

δ 8.48(brs, 1H), 7.37–6.82(m, 14H), 4.77(t, J=5.0 Hz, 1H), 3.94(dd, J=5.8, 13.7 Hz, 1H), 3.80–3.42(m, 5H), 3.00

(d, J=14.7 Hz, 1H), 2.66(d, J=14.7 Hz, 1H), 2.53(q, J=7.6 Hz, 2H), 2.17(s, 3H), 1.20–1.05(m, 9H).

Aldehyde Intermediate 3R)-1-(formylmethyl)-3-((4-methylphenyl)aminocarbonylmethyl)-3-(N'-(4-methylphenyl)ureido)indolin-2-one Water (10 mL) and concentrated hydrochloric acid (3 mL) were added to an acetone (30 mL) solution of (+)-1-(2,2-diethoxyethyl)-3-((4-methylphenyl) aminocarbonylmethyl)-3-(N'-(4-methylphenyl)ureido)indolin-2-one (compound described in "Example 174(2)" of Japanese Patent Application Laid-Open No. 7-48349, 610 mg), and the mixture was heated to reflux for 2 hours. After allowing the reaction solution to cool, the solvent was removed under reduced pressure for concentration. Dichloromethane was added to the residue, and this was washed twice with saline. After drying the organic layer on anhydrous magnesium sulfate (15–30° C.), it was concentrated under reduced pressure to obtain 529 mg of the title compound as a crude product.

NMR ($CDCl_3$, 270 MHz)

δ 9.71(s, 1H), 7.75(s, 1H), 7.40(s, 1H), 7.38-6.90(m, 11H), 6.65(d, J=7.9 Hz, 1H), 4.76(d, J=18.7 Hz, 1H), 4.40(d, J=18.7 Hz, 1H), 2.98(d, J=14.5 Hz, 1H), 2.55(d, J=14.5 Hz), 2.30(s, 3H), 2.23(s, 3H).

Compound E

3R)-1-(2,2-diisopropoxyethyl)-3-((4-methylphenyl)aminocarbonylmethyl)-3-(N'-(4-methylphenyl)ureido)indolin-2-one The aldehyde intermediate obtained above (60 mg) was dissolved in isopropanol (10 mL), para-toluenesulfonic acid (10 mg) was added, and the mixture was heated to reflux for 4 hours. After allowing the reaction solution to cool, the solvent was removed under reduced pressure for concentration. The residue was diluted with dichloromethane and washed with saturated bicarbonate water. After drying the organic layer on anhydrous magnesium sulfate (15–30° C.), it was concentrated under reduced pressure. The residue was purified by silica gel column chromatography (hexane/ethyl acetate=1/1) to obtain 46 mg of the title compound (yield: 62%).

NMR ($CDCl_3$, 270 MHz)

δ 8.37(s, 1H), 7.39–6.90(m, 13H), 6.79(s, 1H), 4.84(dd, J=4.9, 4.7 Hz, 1H), 3.94–3.73(m, 4H), 3.00(d, J=14.9 Hz, 1H), 2.58(d, J=14.9 Hz, 1H), 2.29(s, 3H), 2.22(s, 3H), 1.18(d, J=6.3 Hz, 6H), 1.11–1.04(m, 6H).

Compound F

3R)-1-(2,2-bis(2-fluoroethoxy)ethyl)-3-((4-methylphenyl) aminocarbonylmethyl)-3-(N'-(4-methylphenyl)ureido)indolin-2-one The aforementioned aldehyde intermediate (50 mg) was dissolved in 2-fluoroethanol (1 mL), camphorsulfonic acid (5 mg) was added, and the mixture was heated to reflux for 5 hours. After allowing the reaction solution to cool, toluene was added and the mixture was concentrated under reduced pressure while azeotropically distilling off the excess 2-fluoroethanol. The residue was diluted with dichloromethane and washed with saturated bicarbonate water. After drying the organic layer on anhydrous magnesium sulfate (15–30° C.), it was concentrated under reduced pressure. The residue was purified by silica gel column chromatography (hexane/ethyl acetate=2/1) to obtain 25 mg of the title compound (yield: 41%).

NMR ($CDCl_3$, 270 MHz)

δ 7.79(s, 1H), 7.32–6.93(m, 13H), 6.76(s, 1H), 5.01–4.96 (m, 1H), 4.62–4.53(m, 2H), 4.45–4.35(m, 2H), 4.11(dd, J=6.6, 14.3 Hz, 1H), 4.00–3.72(m, 5H), 2.88(d, J=14.5 Hz, 1H), 2.49(d, J=14.5 Hz, 1H), 2.30(s, 3H), 2.23(s, 3H).

Compound G

3R)-1-(2,2-bis(2-chloroethoxy)ethyl)-3-((4-methylphenyl) 3-(N'-(4-methylphenyl)ureido)indolin-2-one The aforementioned aldehyde intermediate (50 mg) was dissolved in 2-chloroethanol (1 mL), camphorsulfonic acid (5 mg) was added, and the mixture was stirred at 90° C. for 5 hours. After allowing the reaction solution to cool, toluene was added and the mixture was concentrated under reduced pressure while azeotropically distilling off the excess 2-chloroethanol. The residue was diluted with dichloromethane and washed with saturated bicarbonate water. After drying the organic layer on anhydrous magnesium sulfate (15–30° C.), it was concentrated under reduced pressure. The residue was purified by silica gel column chromatography (hexane/ethyl acetate=2/1) to obtain 15 mg of the title compound (yield: 23%).

NMR ($CDCl_3$, 270 MHz)

δ 7.88(s, 1H), 7.32–6.93(m, 13H), 6.79(s, 1H), 4.96–4.91 (m, 1H), 3.97–3.46(m, 10H), 2.98(d, J=14.5 Hz, 1H), 2.49(d, J=14.5 Hz, 1H), 2.30(s, 3H), 2.23(s, 3H).

Synthesis Example 3

Racemic forms of compound H and compound I, and an optically active form of compound I, were synthesized by the following method.

Compound H

3R)-1-(2,2-diethoxyethyl)-3-(4-hydroxymethylphenyl) aminocarbonylmethyl-3-(N'-(4-methylphenyl)ureido) indolin-2-one (+)-1-(2,2-diethoxyethyl)-3-hydroxycarbonylmethyl-3-(N'-(4-methylphenyl)ureido)indolin-2-one (compound described in "Example 174(1)" of Japanese Patent Application Laid-Open No. 7-48349, 300 mg) was dissolved in acetonitrile (10 mL), and after adding p-aminobenzylalcohol (100 mg) and 1-ethyl-3-(3-dimethylaminopropyl)-carbodiimide hydrochloride (151 mg) in that order, the mixture was stirred at 15–30° C. for 18 hours. Water was added to the reaction solution, extraction was performed with ethyl acetate, the organic layer was dried with anhydrous sodium sulfate and the solvent was distilled off. The resulting reaction mixture was purified by column chromatography to obtain 324 mg of the title compound (yield: 88%).

$^1$H-NMR ($CDCl_3$, 200 MHz)

δ 8.83(s, 1H), 7.40–6.84(m, 14H), 4.78(t, J=5.6 Hz, 1H), 4.51(s, 2H), 3.99(dd, J=5.9 Hz, 14.2 Hz, 1H), 3.83–3.45(m, 5H), 2.90(d, J=15.2 Hz, 1H), 2.67(broad s, 1H), 2.60(d, J=15.2 Hz, 1H), 1.15(t, J=6.9 Hz, 3H), 1.10(t, J=6.9 Hz, 3H).

IR (KBr, $cm^{-1}$)

3330, 2980, 1708, 1671, 1610, 1533, 1478, 1464, 1412, 1375, 1310, 1248, 1209, 1125, 1059, 818, 751, 475.

MS (EI, 70 ev)

m/e=560 ($M^+$), 514, 486, 453.

Urea Intermediate 3-(N'-(4-t-butyldimethylsilyloxymethylphenyl)ureido)-1-(2,2-diethoxyethyl)indolin-2-one A dichloromethane solution containing p-aminobenzyl-t-butyldimethylsilylether (1.63 g) was slowly added dropwise to a dichloromethane solution containing triphosgene (681 mg) at 15–30° C., and then a dichloromethane solution containing triethylamine (1.92 mL) was added and the mixture was stirred for one hour to prepare a dichloromethane solution containing an isocyanate compound.

1-(2,2-diethoxyethyl)-3-(hydroxyimino)indolin-2-one (compound mentioned as an intermediate in Example 28 of Japanese Patent Application Laid-Open No. 7-48349, 2.014 g) was dissolved in methanol, 10% Pd carbon was added and the mixture was stirred for 4 hours under a hydrogen atmosphere at 15–30° C. After filtering the reaction mixture to remove the Pd carbon, the filtrate was concentrated. The residue was dissolved in dichloromethane and then added on ice to the already prepared isocyanate compound-containing dichloromethane solution. After stirring at the same temperature for one hour, water was added to the reaction solution, extraction was performed with dichloromethane, the organic layer was dried with anhydrous sodium hydrogensulfate and the solvent was distilled off. The reaction mixture was purified by column chromatography to obtain 2.454 g of the title compound (yield: 68%).

$^1$H-NMR (CDCl$_3$, 200 MHz)

δ 7.58(broad s, 1H), 7.44–6.95(m, 9H), 6.03(broad d, J=5.7 Hz, 1H), 5.21(d, J=6.6 Hz, 1H), 4.70(t, J=5.1 Hz, 1H), 4.63(s, 2H), 3.96(dd, J=5.1 Hz, 13.7 Hz, 1H), 3.83–3.42(m, 5H), 1.15(t, J=6.9 Hz, 6H), 0.94(s, 9H), 0.09(s, 6H).

Amide Intermediate 3-(N'-(4-t-butyldimethylsilyloxymethylphenyl) ureido-1-(2,2-diethoxyethyl)-3-((4-methylphenyl) aminocarbonylmethyl)indolin-2-one 3-(N'-(4-t-butyldimethylsilyloxymethylphenyl)ureido)-1-(2,2-diethoxyethyl)indolin-2-one (1 g) was dissolved in dimethylformamide (15 mL), potassium t-butoxide (237 mg) was added at 15–30° C., and after stirring the mixture for one minute, N-paratolyl-2-bromoacetamide (460 mg) was added. After stirring for 15 minutes, water was added, extraction was performed with ethyl acetate, the organic layer was dried with anhydrous sodium hydrogensulfate and the solvent was distilled off. The reaction mixture was purified by silica gel column chromatography to obtain 939 mg of the title compound (yield: 73%).

$^1$H-NMR (CDCl$_3$, 200 MHz)

δ 8.52(s, 1H), 7.40–6.92(m, 14H), 4.78(t, J=5.7 Hz, 1H), 4.60(s, 2H), 4.02(dd, J=5.7 Hz, 14.9 Hz, 1H), 3.87–3.46(m, 5H), 3.00(d, J=14.9 Hz, 1H), 2.67(d, J=14.9 Hz, 1H), 2.30(s, 3H), 1.17(t, J=7.4 Hz, 3H), 1.13(t, J=7.4 Hz, 3H), 0.92(s, 9H), 0.06(s, 6H).

Compound I (Racemic Form)

1-(2,2-diethoxyethyl)-3-(N'-(4-hydroxymethylphenyl)ureido)-3-((4-methylphenyl) aminocarbonylmethyl)indolin-2-one 3-(N'-(4-t-butyldimethylsilyloxymethylphenyl)ureido)-1-(2,2-diethoxyethyl)-3-((4-methylphenyl) aminocarbonylmethyl) indolin-2-one (308 mg) was dissolved in ethanol (15 mL), concentrated sulfuric acid (10 mg) was added, and the mixture was stirred at 15–30° C. for one hour. Water was added to the reaction solution, extraction was performed with ethyl acetate, the organic layer was dried with anhydrous sodium hydrogensulfate and the solvent was distilled off. The reaction mixture was purified by silica gel column chromatography to obtain 225 mg of the title compound (yield: 88%).

$^1$H-NMR (CDCl$_3$, 270 MHz)

δ 8.13(s, 1H), 7.37–6.90(m, 14H), 4.79(broad s, 1H), 4.50(s, 2H), 4.01(dd, J=5.9 Hz, 14.5 Hz, 1H), 3.86–3.46(m, 6H), 2.96(d, J=14.8 Hz, 1H), 2.53(d, J=14.8 Hz, 1H), 2.29(s, 3H), 1.16(t, J=7.3 Hz, 3H), 1.11(t, J=6.9 Hz, 3H).

IR (KBr, cm$^{-1}$)

3365, 3000, 1717, 1702, 1621, 1545, 1521, 1498, 1480, 1420, 1388, 1321, 1263, 1137, 1069, 831, 763, 515, 484.

MS (EI, 70 eV)

m/e=560(M$^+$), 515, 392, 365, 306, 292.

Ester Intermediate 1-(2,2-diethoxyethyl)-3-(N'-(4-t-butyldimethylsilyloxymethylphenyl)ureido)-3-((L-menthoxy)carbonylmethyl)indolin-2-one A hexane solution containing one equivalent of n-butyl lithium (1.68 M, 1.0 mL) was slowly added to a dry tetrahydrofuran (20 mL) solution containing 3-(N'-(4-t-butyldimethylsilyloxymethylphenyl)ureido)-1-(2,2-diethoxyethyl)indolin-2-one (936 mg) while cooling on ice under a nitrogen stream, and after stirring the mixture at the same temperature for 10 minutes, a dry tetrahydrofuran solution (10 mL) containing L-menthyl bromoacetate (542 mg) was added dropwise. After stirring the mixture at 0° C. for 8 hours, it was poured into saline and extraction was performed with ethyl acetate. The organic layer was dried on anhydrous sodium sulfate and then concentrated, and the residue was purified by silica gel column chromatography (elution with hexane/ethyl acetate=3/1) and recrystallized from methanol water to obtain 357 mg of the title compound (yield: 28%).

$^1$H-NMR (CDCl$_3$, 270 MHz)

δ 7.30–6.97(m, 8H), 6.81(brs, 1H), 6.76(brs, 1H), 4.74 (dd, J=5.7 Hz, 4.9 Hz, 1H), 4.69–4.61(m, 3H), 3.94(dd, J=6.9 Hz, 14.2 Hz, 1H), 3.86–3.49(m, 5H), 2.99(d, J=15.2 Hz, 1H), 2.59(d, J=15.2 Hz, 1H), 1.92-1.90(brs, 1H), 1.21–1.10(m, 6H), 0.92(s, 9H), 1.36-0.65(m, 18H), 0.065(s, 6H).

Compound I (Optically Active Form)

1-(2,2-diethoxyethyl)-3-(N'-(4-hydroxymethylphenyl)ureido)-3-((4-methylphenyl) aminocarbonylmethyl)indolin-2-one An aqueous potassium hydroxide solution (1N, 1.36 mL) was added to an ethanol (8 mL) solution containing 1-(2,2-diethoxyethyl)-3-(N'-(4-t-butyldimethylsilyloxymethylphenyl) ureido)-3-((L-menthoxy)carbonylmethyl)indolin-2-one (293 mg) at 15–30° C., and after stirring the mixture at 70° C. for 4 hours, it was concentrated. After adding water to the residue and washing with chloroform, 2N hydrochloric acid was added thereto to acidify. The resulting insoluble portion was extracted with ethyl acetate, and after washing the organic layer with saline, it was dried on anhydrous sodium sulfate and concentrated to obtain 234 mg of 1-(2,2-diethoxyethyl)-3-hydroxycarbonylmethyl-3-(N'-(4-hydroxymethylphenyl) ureido) indolin-2-one (carboxylic acid intermediate) as a crude product.

The carboxylic acid intermediate (234 mg) was dissolved in dichlormethane (10 mL), and 1-ethyl-3-(3-dimethylaminopropyl)-carbodiimide hydrochloride (131 mg) and para-toluidine (73 mg) were added in that order. The mixture was stirred at 15–30° C. for 18 hours and concentrated. After diluting the residue with ethyl acetate and washing it with dilute hydrochloric acid and saturated bicarbonate water, it was dried on anhydrous sodium sulfate and concentrated. The crude product was purified by silica gel column chromatography (elution with hexane/ethyl acetate=2/1) to obtain 204 mg of a white powder (90% ee, 80% yield from ester intermediate).

A 140 mg portion of this powder was purified by preparative high performance liquid chromatography using an optically active column, to obtain the R-form (117 mg, $[\alpha]_D^{26}=94°$, C=1.014/MeOH) and S-form (7 mg).
<Separation Conditions>
Column: SUMICHIRAL OA-4800

20 mm diameter×25 cm length Detection wavelength: UV 254 nm Flow rate: 20 mL/min Solvent: Hexane/1,2-dichloroethane/methanol=75/22/3 Retention time: S-form: 24 minutes, R-form: 40 minutes Example 1

Chondrogenesis Promoting Effect with Oral Administration to Healthy Rats

"Compound A" obtained in Synthesis Example 1 above was suspended in a 3% gum Arabic solution and orally administered to 6-week-old male SD rats (Nihon SLC Corp./Nihon Charles River Corp.) at a dosage of 2 g/kg/day for 4 weeks.

Each rat was then autopsied, the auricula, trachea, sternum, femoral/crural knee joint and lumbar spine (disk) were immersed for one week in 20% neutral buffer formalin (Wako Pure Chemical Industries, Co., Ltd.) and fixed, the sternum, femoral/crural knee joint and lumbar spine (disk) were then demineralized for 2 weeks with a 20% EDTA-4Na solution (pH 7.4, Wako Pure Chemical Industries), and observation sites were trimmed with a razor (Feather Co., Ltd.). Observation sites were trimmed from the auricula and trachea with a razor without demineralization.

Each of the trimmed tissue samples was prepared into a paraffin embedded block using an automatic embedding apparatus (Sakura Corp.) and paraffin (equivalent mixture of products by Kokusan Kagaku Corp. and Fisher Scientific Corp.). Here, a paraffin automatic dispensing embedding center (Miles Scientific Corp.) was used to fix each paraffin block in a tissue sample cassette (TISSUE-TEK Corp.)

The paraffin block was cut into 2 μm-thick sections using a microtome (Daiwa Optical Instruments Corp.) and microtome knife (Feather Co., Ltd.), and then attached onto slide glass (Matsunami Glass Corp.) and dried. After drying, the sections were dipped in xylene to remove the paraffin, and then dipped in a step dilution series from ethanol to water and then stored in water. The sections were stained with 0.2% hematoxylin and 0.1% eosin (both from Merck Co., Ltd.), and then mounted with a mounting agent (Takefuji Chemical Co., Ltd.) and a cover glass (Matsunami Glass Corp.) and observed under a microscope (magnification: 10× object lens, product of Nihon Kogaku Corp.). The femoral strip was stained with 0.3% Safranin O (Merck Co., Ltd.) for histochemical analysis of promoted formation of hyaline cartilage, and was observed under a microscope in the same manner (magnification: 10× object lens). The results are shown in the photomicrographs of FIGS. 1A–5A and FIGS. 1B–5B.

As clearly seen in these photomicrographs taken after staining, no chondrogenesis promoting effect was found in the vehicle control group (rats orally administered 3% gum Arabic alone) (FIGS. 1A, 2A, 3A, 4A and 5A), but all the rats in the group administered "compound A" had accelerated hyaline cartilage formation in all of the organs (FIGS. 1B, 2B, 3B, 4B and 5B).

The results of the experiment confirmed that compound A exhibits a chondrogenesis promoting effect in vivo.

Example 2

Chondrogenesis Promoting Effect with Administration into Rat Knee Joints

A 27G injection needle and 1 mL syringe (both by Terumo Corp.) were used to administer 1 mmol/L of "compound A" (dissolved in 50% DMSO dimethylsulfoxide)-physiological saline solution; DMSO by Junsei Chemical Corp., physiological saline by Otsuka Pharmaceutical Corp.) into the right knee joint of 10-week-old male SD rats (Nihon Charles River Corp.) at a dosage of 50 μL per day for 3 weeks.

Another test group was administered 50% DMSO-physiological saline (by Junsei Chemical Corp. and Otsuka Pharmaceutical Corp., respectively) in the same manner as a vehicle control.

After 3 weeks of daily administration, the rats were autopsied, and the distance between lateral and medial attachment sites of collateral ligament of the right femur was measured with calipers (Mitsutoyo Corp.) to determine the width of the femoral knee joint. Then, in the same manner as Example 1, tissue samples were prepared and stained with 0.3% Safranin O (Merck Co., Ltd.) and observed under a microscope (magnification: 10× object lens, product of Nihon Kogaku Corp.). The results are shown in FIGS. 6, 7A and 7B.

Figure 6:
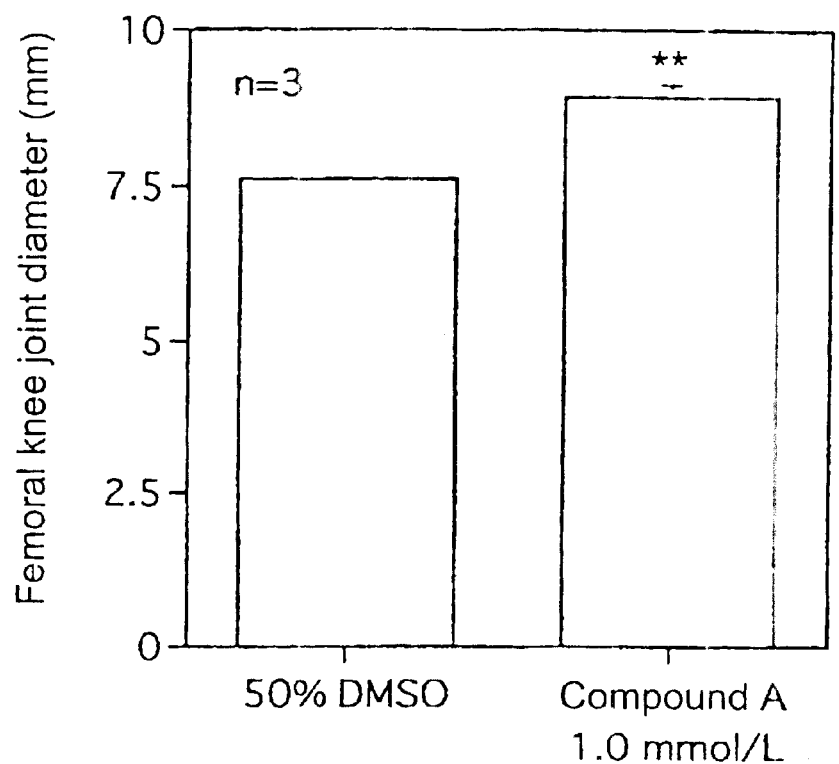
FIG. 6 is a graph of the width of the femoral knee joint of a rat after repeated administration of compound A (1.0 mmol/L) or a vehicle control (50% DMSO physiological saline solution) at 50 µl per day into the knee joint for 3 weeks.
Figure 7A:
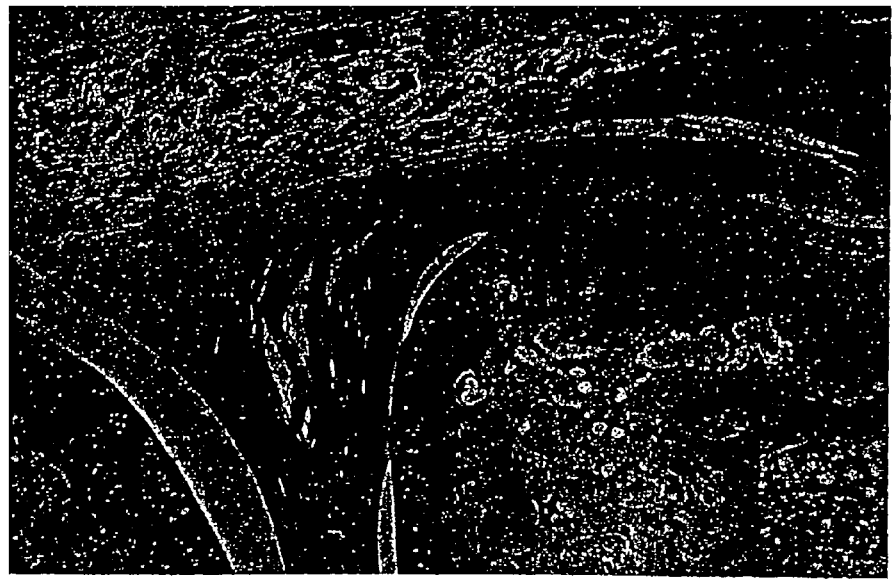
FIG. 7A is a photomicrograph showing a 0.3% Safranin O stained femoral knee joint tissue sample from a rat after repeated administration of a vehicle control (50% DMSO physiological saline solution) at 50 µl per day into the knee joint for 3 weeks.
Figure 7B:
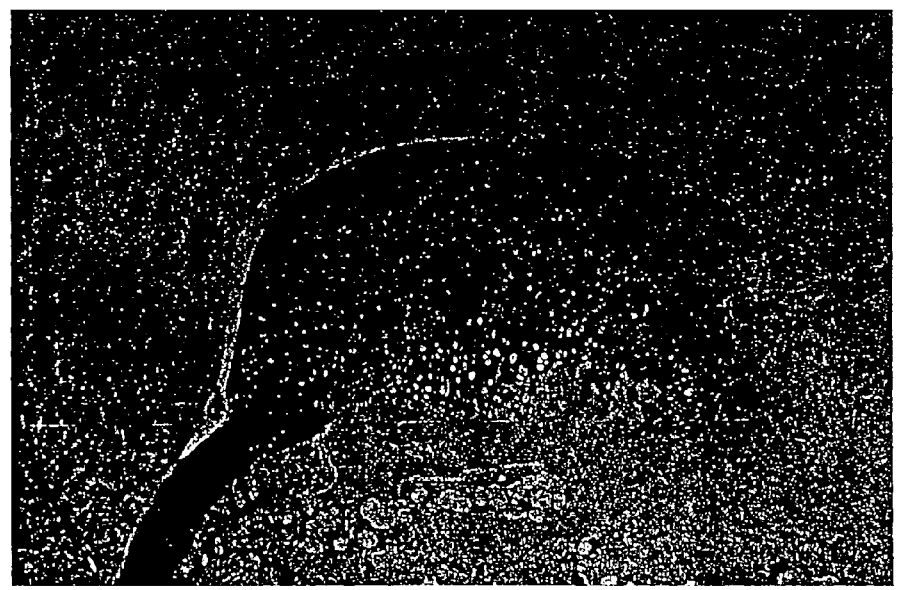
FIG. 7B is a photomicrograph showing a 0.3% Safranin O stained femoral knee joint tissue sample from a rat after repeated administration of compound A (1.0 mmol/L) at 50 µl per day into the knee joint for 3 weeks.

As shown in FIG. 6, the femoral knee joint widths were significantly larger in the group administered compound A than in the vehicle control group. As shown in FIGS. 7A and 7B, histological observation revealed Safranin O-positive accelerated formation of cartilage tissue.

The results of the experiment confirmed that compound A exhibits a chondrogenesis promoting effect even with local administration, such as intraarticular injection.

Example 3

Effect of Compound A on Rat Primary Culture Articular Chondrocytes

Articular chondrocytes were trimmed from the femoral knee joint of 6-week-old male SD rats (Nihon SLC Corp.) using a scalpel, and then digested in 0.3% collagenase (WORTHINGTON Corp.) and cultivated (Calcif. Tissue Int. 19:179–187,1975).

The isolated articular chondrocytes were used to measure glycosaminoglycan synthesis in the cartilage matrix by measurement of the uptake of $^{35}S$-labeled sulfuric acid (Amersham Co., Ltd.) into glycosaminoglycan. Specifically, the articular chondrocytes were cultured in a 96-well cell culturing plate (FALCON Corp.) to a cell density of 10,000 per well. The medium used was an equivalent mixture of Dulbecco MEM containing fetal bovine serum (final concentration: 10%), 100 U/mL of penicillin (Meiji Seika Co., Ltd.) and 100 μg/mL of streptomycin (Banyu Pharmaceutical Corp.), and Ham F-12 medium (both by GIBCO Corp.).

When the chondrocytes reached confluency, the medium was exchanged with one having a serum concentration of 0.3% and culturing was carried out overnight, after which the medium was exchanged with the same type also containing 10 μmol/L of compound A, and then after 3 hours, $^{35}$S-labeled sulfuric acid (Amersham Co., Ltd.) was added at 0.5 μCi per well and culturing was carried out for 24 hours. The medium was then collected in a 24-well plate and stored at 4° C. The cell layer was digested at 37° C. overnight (16 hours) by addition of 0.1 mL of 2 mg/mL Actinase E (Kaken Pharmaceutical Co., Ltd.) per well. On the following day the digested cell layer was combined with the stored medium, and after addition of 0.1 mL of 0.1 mg/mL chondroitin sulfate C (Sigma Corp.), 0.5 mL of 2 mmol/L MgSO$_4$ (Wako Pure Chemical Industries), 0.5 mL of 0.2 mol/L Tris/HCl (Sigma Corp.) and 0.5 mL of 1% cetylpyridinium chloride (dissolved in 20 mmol/L sodium chloride solution, Wako Pure Chemical Industries), the mixture was allowed to stand at 37° C. for 2 hours. The sample was then filtered with glass fiber filter paper (Toyo Filter Paper Corp.), the filter paper was washed 3 times with 2 mL of 1% cetylpyridinium chloride (20 mmol/L), one each was placed in a liquid scintillation counting vial (PACKARD Corp.), 10 mL of scintillator (Nacalai Tesque Corp.) was poured in, and the radioactivity was measured with a liquid scintillation counter (PACKARD Corp.).

Figure 8:
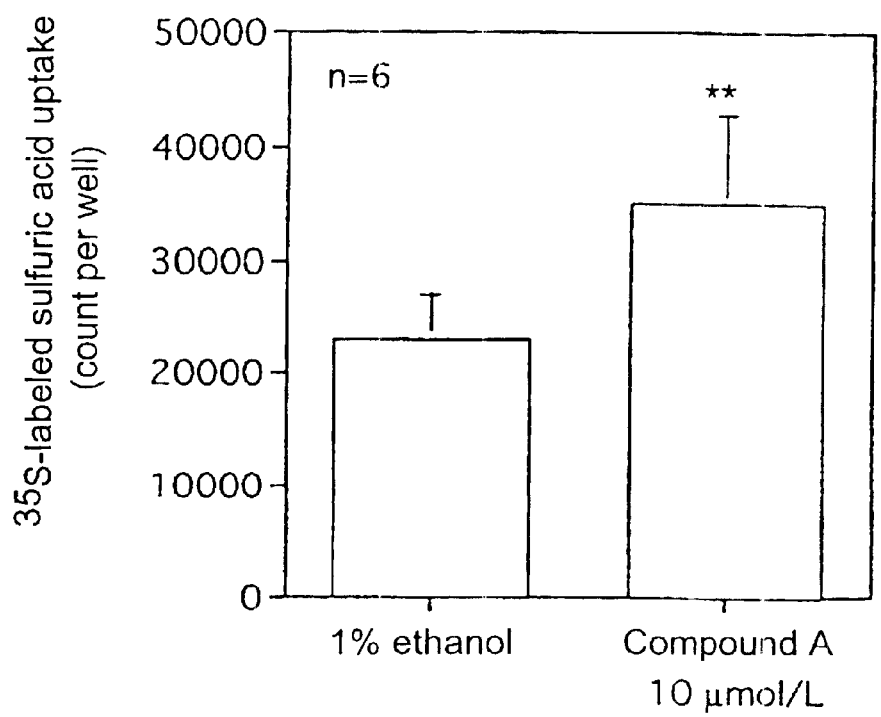
FIG. 8 is a graph showing the uptake of $^{35}$S-labeled sulfuric acid into glycosaminoglycans in rat primary culture articular chondrocytes to which compound A or a vehicle control (ethanol at 1% final concentration in medium) was added.
Figure 9:
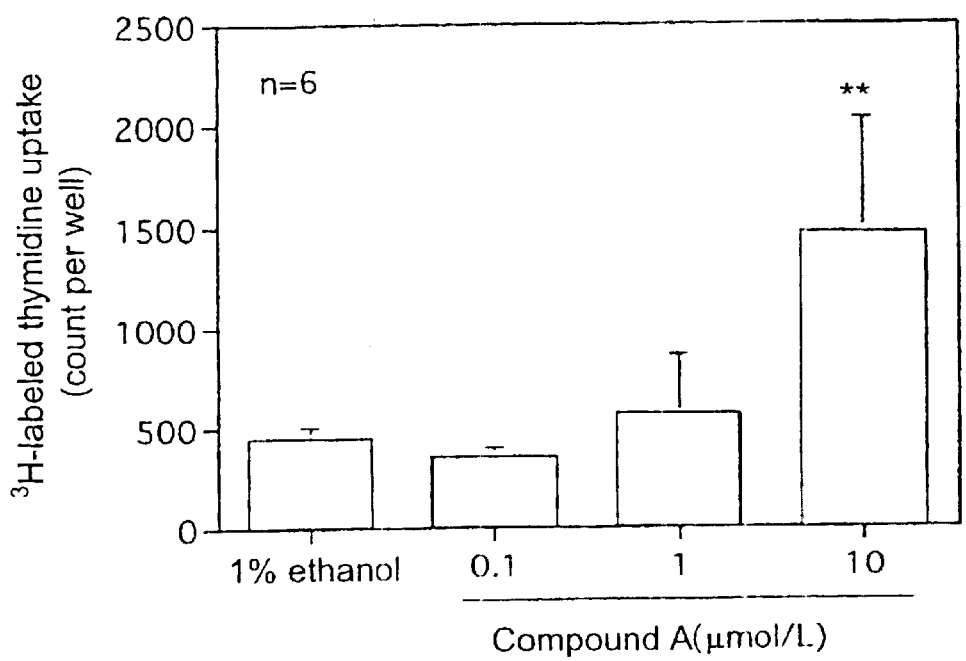
FIG. 9 is a graph showing the uptake of $^3$H-labeled thymidine in rat primary culture articular chondrocytes to which compound A or a vehicle control (ethanol at 1% final concentration in medium) was added.

Uptake of $^3$H-labeled thymidine (Amersham Corp.) was measured to determine the cell growth. For the measurement, the isolated articular chondrocytes were cultured in a 96-well cell culturing plate (FALCON Corp.) to a cell density of 10,000 per well. The medium used was an equivalent mixture of Dulbecco MEM containing fetal bovine serum (final concentration: 10%), 100 U/mL of penicillin (Meiji Seika Co., Ltd.) and 100 μg/mL of streptomycin (Banyu Pharmaceutical Corp.), and Ham F-12 medium (both by GIBCO Corp.). After 60–70% of the cells reached confluency, the medium was exchanged with one having a fetal bovine serum concentration of 0.3% and culturing was carried out overnight. On the following day, the medium was exchanged with the same type also containing compound A at a final concentration of 0.1, 1.0 or 10 μmol/L and 0.3% fetal bovine serum. After 24 hours, $^3$H-labeled thymidine (Amersham Co., Ltd.) was added at 1 μCi per well and culture was carried out for 4 hours, after which the medium was discarded and a cell collecting apparatus (SKATRON Corp.) was used to collect the cell layer on scintillation counter glass fiber filter paper (Wallac Corp.). The filter paper was soaked with plastic scintillator (Wallac Corp.), and the radioactivity was measured with a scintillation counter (Wallac Corp.). The results are shown in the graphs of FIGS. 8 and 9.

Uptake of $^{35}$S-labeled sulfuric acid was significantly increased by addition of 01 μmol/L of compound A, with respect to the ethanol at 1% final concentration in the medium, as the control solvent. Uptake of $^3$H-labeled thymidine was also significantly increased by addition of 10 μmol/L of compound A with respect to the control solvent.

These results confirmed that compound A has an effect of increasing cartilage matrix synthesis and chondrocyte growth. The chondrogenesis promoters represented by general formula (I) may also be used as agents to promote the extracellular matrix synthesis and growth properties of chondrocytes before or after chondrocyte transplantation, such as autogenous chondrocyte transplantation.

Example 4

Effect of compound A on Differentiation of the Common Mouse Chondrocyte and Adipocyte Precursor Cell Line (CL-1) into Chondrocytes Chondrocytes established from normal adult mice and the adipocyte line CL-1 (WO98/39414) were cultured in a 4-well chamber slide (Nunc Corp.) to a cell density of 5000/cm$^2$. The medium used was A-MEM (GIBCO Corp.) containing 100 U/mL of penicillin (Meiji Seika Co., Ltd.), 100 μg/mL of streptomycin (Banyu Pharmaceutical Corp.) and 10% fetal bovine serum (INTERGEN Corp.). When the CL-1 cells reached confluency, compound A was added to a final concentration of 10 μmol/L, with further addition when the medium was exchanged 3 times a week during culturing for 7 days.

Figure 10A:
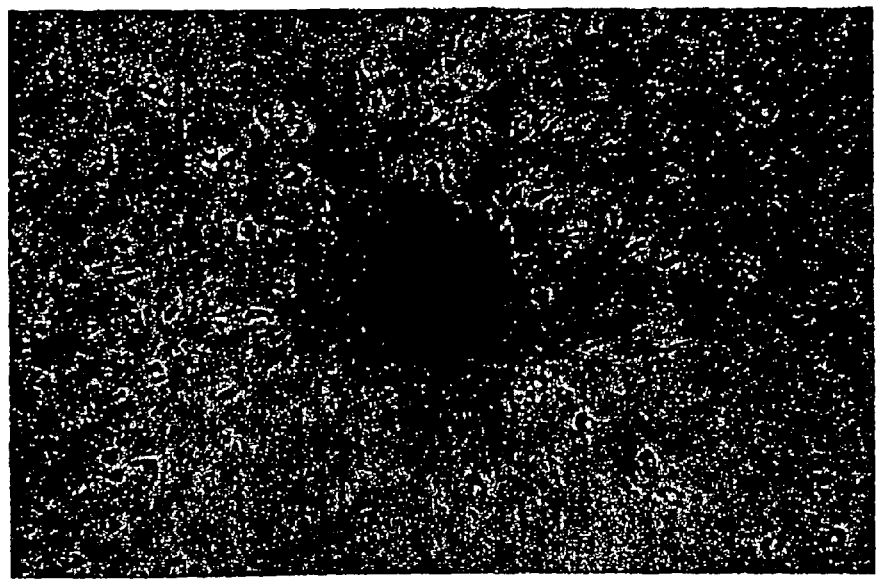
FIG. 10A is a photomicrograph showing alcian blue/oil red O double stained confluent CL-1 cells after addition of a vehicle control (ethanol at 1% final concentration in medium) and culturing for 7 days.
Figure 10B:
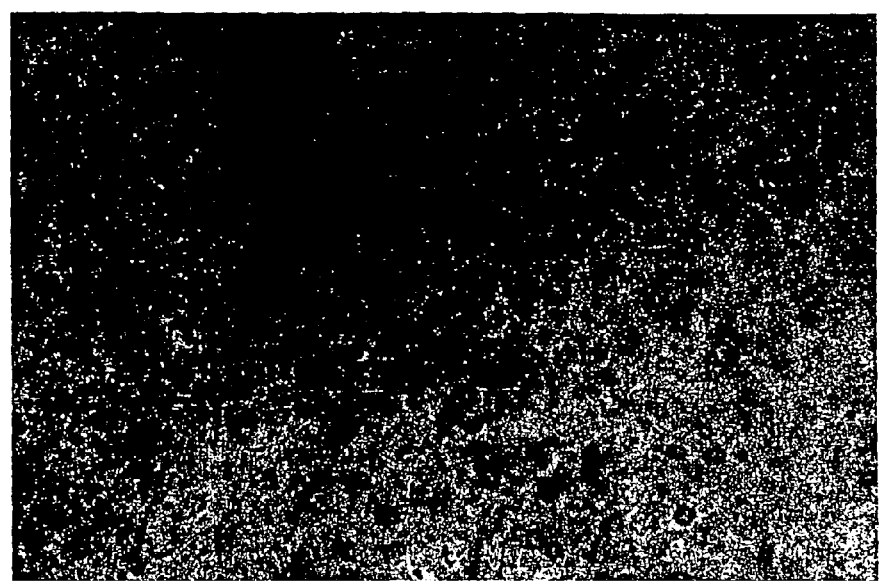
FIG. 10B is a photomicrograph showing alcian blue/oil red O double stained confluent CL-1 cells after addition of compound A (10 µmol/l final concentration in medium) and culturing for 7 days.

A slide was also prepared with ethanol (Junsei Chemical Corp.) to a final concentration of 1% in the medium as a vehicle control. On the 7th day after confluency, the plates were collected, the CL-1 cell layer was double-stained with alcian blue and oil red O, and differentiation to chondrocytes or adipocytes was observed. After culturing was completed, the cell layer was fixed for one hour at room temperature with a 4% paraformaldehyde solution (Wako Pure Chemical Industries) and then washed with 0.1N hydrochloric acid and stained overnight with an aqueous solution (pH 1.0) of 1% alcian blue (EM Science Corp.). This was washed with 0.1N hydrochloric acid and distilled water and then treated for one minute with an aqueous solution of 85% propylene glycol (Nacalai Tesque Corp.), and stained for 30 minutes in a propylene glycol aqueous solution containing 0.5% oil red O (Merck Co., Ltd.). Subsequent washing with an 85% propylene glycol aqueous solution was followed by washing with distilled water. The nuclei were then stained for 5 minutes with an aqueous solution of 0.3% Kernechtrot (Merck Co., Ltd.). The results are shown in the photomicrographs of FIGS. 10A and 10B. Differentiation of CL-1 to chondrocytes and adipocytes begins after the cells reach confluency, and under ordinary culture conditions, approximately 70% of the cells differentiate to oil red O-positive adipocytes while approximately 30% of the cells differentiate to alcian blue-positive chondrocytes. In FIG. 10A and FIG. 10B, the dark points represent fat droplets in the oil red O-positive fat, and the dark gray areas represent the alcian blue-positive cartilage matrix.

As seen in the photomicrograph after staining in FIG. 10B, compound A clearly promoted differentiation of CL-1 to chondrocytes and suppressed differentiation to adipocytes, compared to the vehicle control (FIG. 10A)

Example 5

Effects of Compounds A, B, C, D, E, F and G on Uptake of $^{35}$S-labeled Sulfuric Acid into the Common Mouse Chondrocyte and Adipocyte Precursor Cell Line (CL-1)

Figure 11:
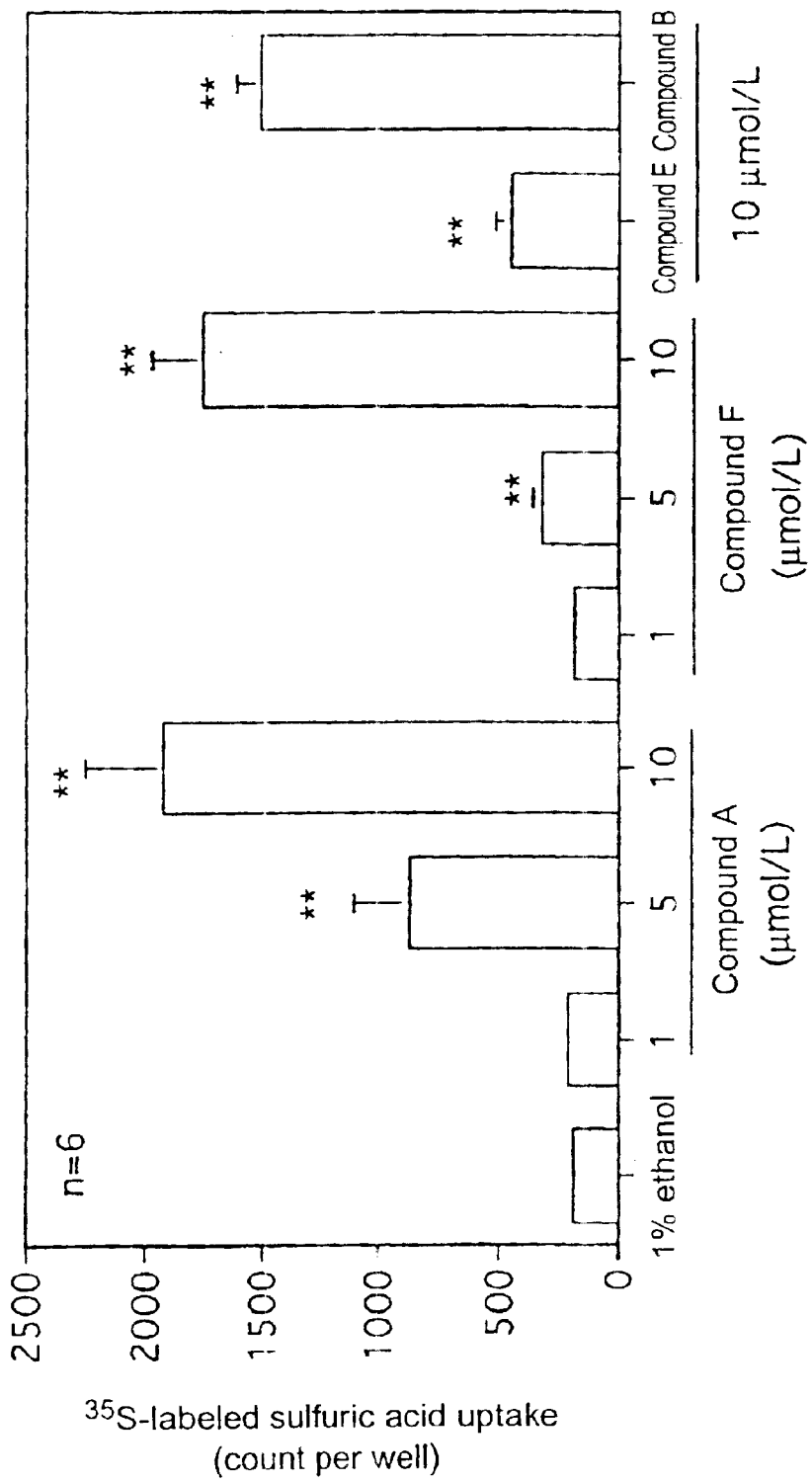
FIG. 11 is a graph showing uptake of $^{35}$S-labeled sulfuric acid into confluent CL-1 cells during the final 24 hours of culturing of the CL-1 cells for 48 hours in medium containing compounds A and F at final concentrations of 1, 5 and 10 μmol/L, compounds B and E at a final concentration of 10 μmol/L or a vehicle control with a final concentration of 1% ethanol.
Figure 12:
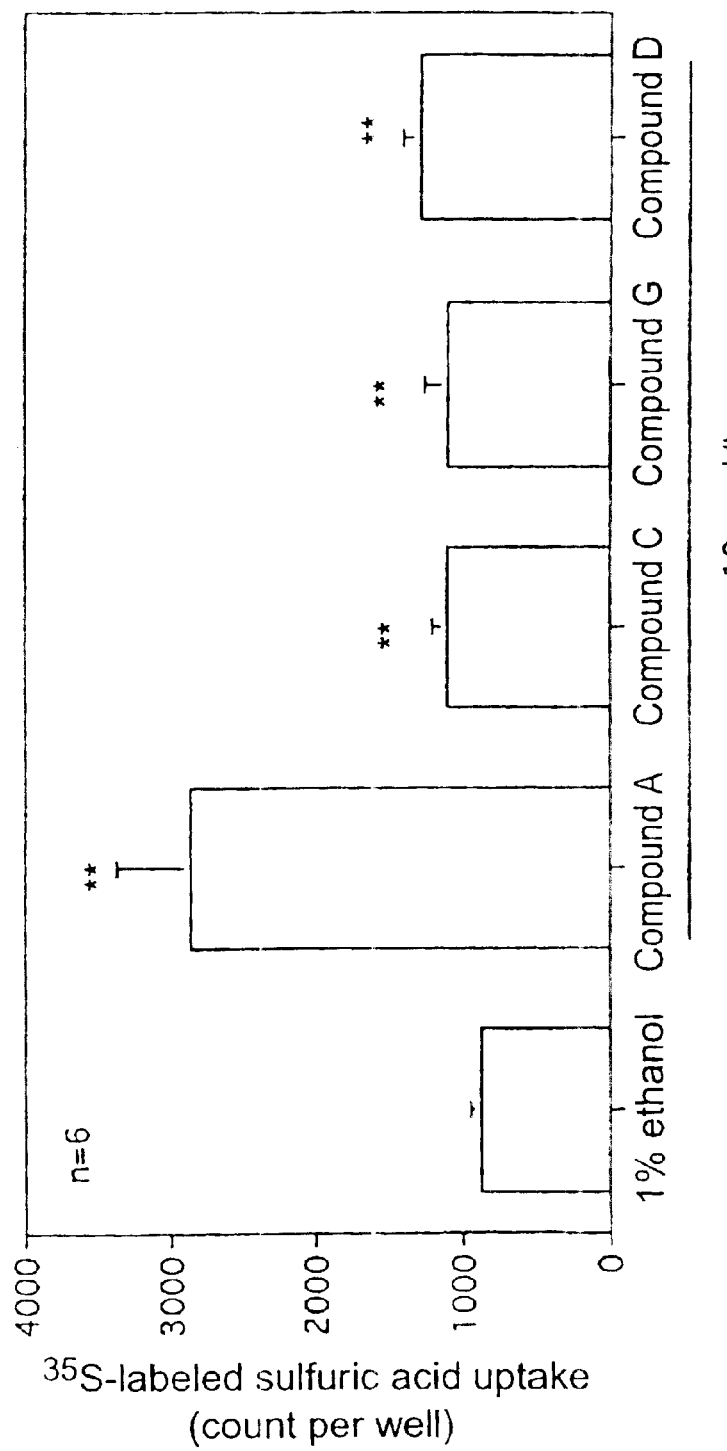
FIG. 12 is a graph showing uptake of $^{35}$S-labeled sulfuric acid into confluent CL-1 cells during the final 24 hours of culturing of the CL-1 cells for 48 hours in medium containing compounds A, C, D and G at final concentrations of 10 μmol/L or a vehicle control with a final concentration of 1% ethanol.

The above-mentioned cell line CL-1 was cultured in a 96-well cell culturing plate (Wallac Corp.) for a liquid scintillation counter (Wallac Corp.) to a cell density of 1000 per well. The medium used was α-MEM (GIBCO Corp.) containing 100 U/mL of penicillin (Meiji Seika Co., Ltd.), 100 μg/mL of streptomycin (Banyu Pharmaceutical Corp.) and 10% fetal bovine serum (INTERGEN Corp.). When the CL-1 cells reached confluency, the medium was exchanged with one containing 10 μmol/L of compounds A, B, C, D, E, F and G, and after 24 hours, $^{35}$S-labeled sulfuric acid was added at 0.5 μCi per well and culturing was continued. For compounds A and F, a medium was also prepared with a concentration of 1 or 5 μmol/L. After 24 hours, the medium was discarded and the cell layer was fixed for 2 hours at room temperature using 0.2 mL of 5% paraformaldehyde (0.1 mol/L phosphate buffer solution (pH 7.4, Wako Pure Chemical Industries) containing 0.4% cetylpyridinium chloride (Wako Pure Chemical Industries). After discarding the fixing solution, it was washed once with the same solution and the washed solution was discarded. After adding 0.1 mL of scintillator (Wallac Corp.) to the cell layer and stirring, the radioactivity was measured with a scintillation counter (Wallac Corp.). The results are shown in FIGS. 11 and 12.

These results indicated that compounds A, B, C, D, E, F and G clearly promote differentiation of CL-1 to chondrocytes and clearly suppress differentiation to adipocytes. The results also show that chondrogenesis promoters represented by general formula (I) may be used as agents to induce differentiation of pluripotent undifferentiated mesenchymal cells (for example, cells with a differentiation state similar to CL-1) into chondrocytes, for treatment of cartilage diseases involving chondrocyte transplantation and the like.

Example 6

Cartilage Repair Effect of Compound A in Full Thickness Cartilage Deficient Rat Models A Kirschner wire with a 2.4 mm diameter (Mizuho Medical Instruments Corp.) was used to create a 2.5 mm-deep deficient area in the right femoral patellar surface, reaching to the marrow, in 10-week-old male CD rats (Nihon Charles River Co., Ltd.). From the seventh day after the operation, 50 μL of a 50% dimethylsulfoxide (DMSO) physiological saline solution as a solvent (DMSO: Junsei Chemical Corp.; physiological saline: Otsuka Pharmaceutical Corp.), or of a 1.0 mmol/L compound A solution, was administered into the right knee joint daily once a day for 3 weeks. The daily dosage of compound A was 81.7 μg.

On the day following the day of final administration, the right femur was taken, and fixed in 20% neutral buffered formaldehyde (Wako Pure Chemical Industries) for one week, and then demineralized for 2 weeks with 20% EDTA-4Na solution (pH 7.4, Wako Pure Chemical Industries), and the deficient area was trimmed with a razor (Feather Co., Ltd.). The trimmed area was subjected to paraffin blocking using an automatic embedding apparatus (Sakura Corp.) and paraffin (equivalent mixture of products by Kokusan Kagaku Corp. and Fisher Scientific Corp.). Here, a paraffin automatic dispensing embedding center (Miles Scientific Corp.) was used to fix each paraffin block in a tissue sample cassette (TISSUE-TEK Corp.)

Each paraffin block was cut into 2 μm-thick sections using a microtome (Daiwa Optical Instruments Corp.) and microtome knife (Feather Co., Ltd.), and then attached onto slide glass (Matsunami Glass Corp.) and dried. After drying, the sections were dipped in xylene to remove the paraffin, and then dipped in a step dilution series from ethanol to water and then stored in water. The sections were stained with 0.3% Safranin O (Merck Co.,.Ltd.) and observed with a microscope (magnification: 10× object lens), and a histological score was assigned according to a modification of the method of Wakitani et al. (J. Bone Joint Surg. 76-A, 579–592, 1994).

Figure 13A:
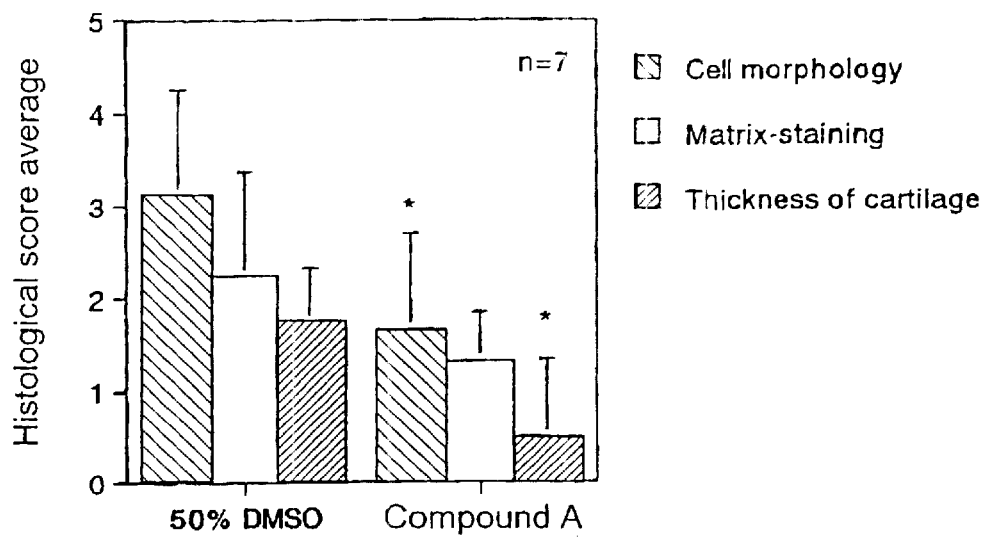
FIG. 13A and FIG. 13B are graphs showing the results from histological examination of cartilage repair in deficient areas of the femoral patellar surface of rats with deficient areas reaching to the marrow were created, given repeated administration of compound A (1.0 mmol/L) or a vehicle control (50% DMSO physiological saline solution) at 50 μL per day for 3 weeks beginning on the 7th day after the operation.
Figure 13B:
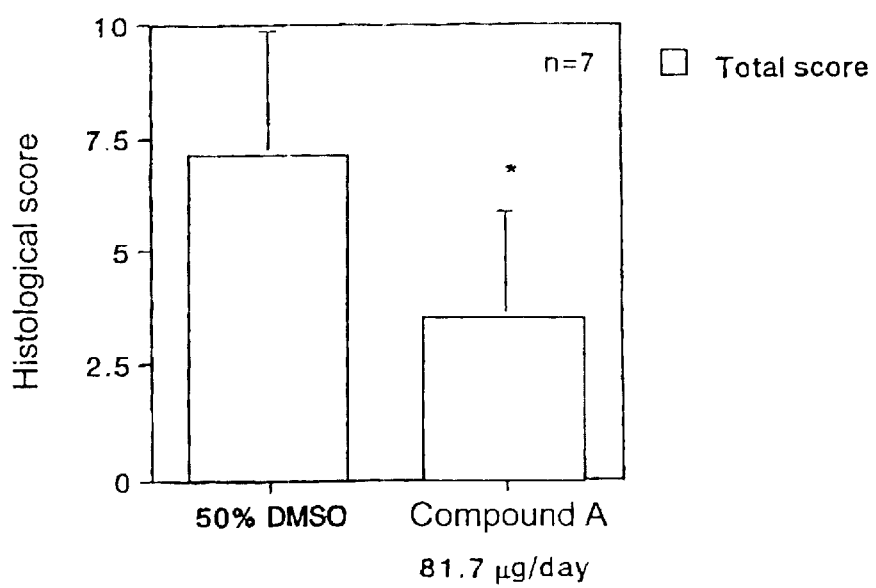
Figure 14A:
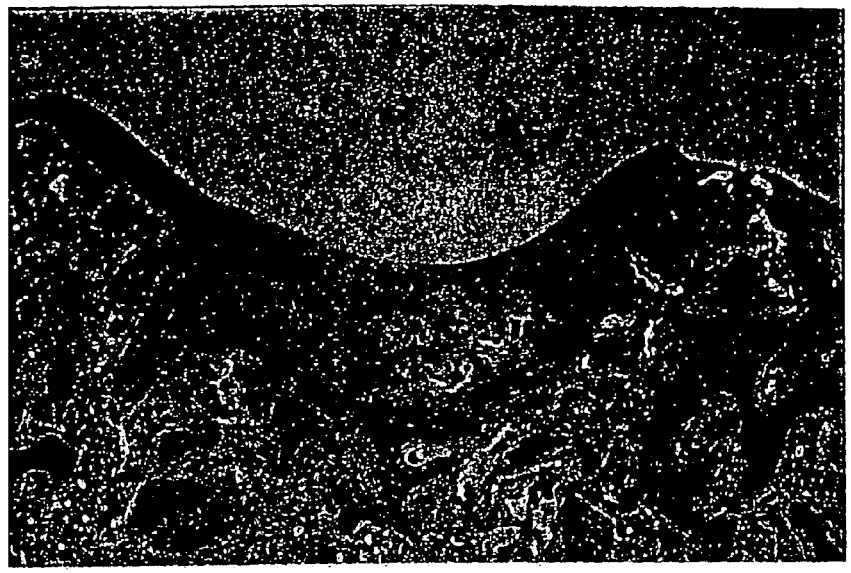
FIG. 14A is a photomicrograph showing a 0.3% Safranin O stained tissue sample of a deficient area created in the femoral patellar surface reaching to the marrow of a rat given repeated intraarticular administration of a vehicle control (50% DMSO physiological saline solution) at 50 μL per day for 3 weeks beginning on the 7th day after the operation.
Figure 14B:
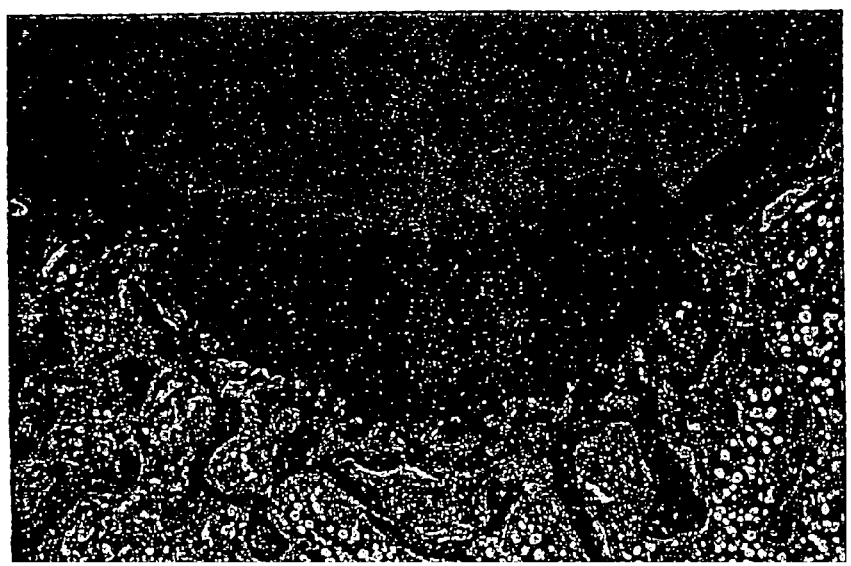
FIG. 14B is a photomicrograph showing a 0.3% Safranin O stained tissue sample of a deficient area created in the femoral patellar surface reaching to the marrow of a rat given repeated intraarticular administration of compound A (1.0 mmol/L) at 50 μL per day for 3 weeks beginning on the 7th day after the operation.

The histological scores of the vehicle control group and compound A-administered group were compared based on the criteria shown in Table 10 below. In the group administered compound A alone, there was a significant decrease in the cell morphology and thickness of cartilage (FIG. 13A) and in the total score (FIG. 13B) compared to the group administered the solvent alone. As shown in FIGS. 14A and 14B, the deficient areas exhibited repair in the Safranin O-positive cartilaginous tissue. These experimental results confirmed that compound A exhibits a cartilage repairing effect against defect or other articular cartilage damage.

TABLE 10

| | Score |
|---|---|
| Cell morphology | |
| Hyaline cartilage | 0 |
| Mostly hyaline cartilage | 1 |
| Mostly fibrocartilage | 2 |
| Mostly non-cartilage | 3 |
| Non-cartilage only | 4 |
| Matrix-staining (Safranin O) | |
| Normal (compared with host adjacent cartilage) | 0 |
| Moderate positive | 1 |
| Mild positive | 2 |
| Negative | 3 |
| Thickness of Cartilage | |
| >2/3 | 0 |
| 1/3–2/3 | 1 |
| <1/3 | 2 |
| Total score | |
| Sum of above scores | 0–9 |

Example 7

Pathology Suppressing Effect of Compound A in a Rabbit Osteoarthritis Model

Rabbit osteoarthritis model was prepared using 12-week-old male NZW rabbits (Kitayama Labes Co., Ltd.), and performing partial menisectomy in right knee, and excision of the lateral collateral ligament and sesamoid ligament, according to the method of Colombo et al. (Arthritis Rheum. 26(7):875–886, 1983). Beginning on the 7th day after the operation, 500 μL of a 50% dimethylsulfoxide (DMSO) physiological saline solution (DMSO: Junsei Chemical Corp., physiological saline: Otsuka Pharmaceutical Corp.) or 3.0 mmol/L of compound A solution was intraarticularly administered once a day into the right knee joint for a period of 3 weeks. The daily dosage of compound A was 816.8 μg.

On the day following the day of final administration, the right femoral distal and crural proximal sections were taken, and the femur was immersed overnight in 2% paraformaldehyde-2.5% glutaraldehyde fixing solution (both by Wako Pure Chemical Industries) for fixation, while the crus was immersed for one week in 20% neutral buffered formalin (Wako Pure Chemical Industries) for fixation.

Figure 15A:
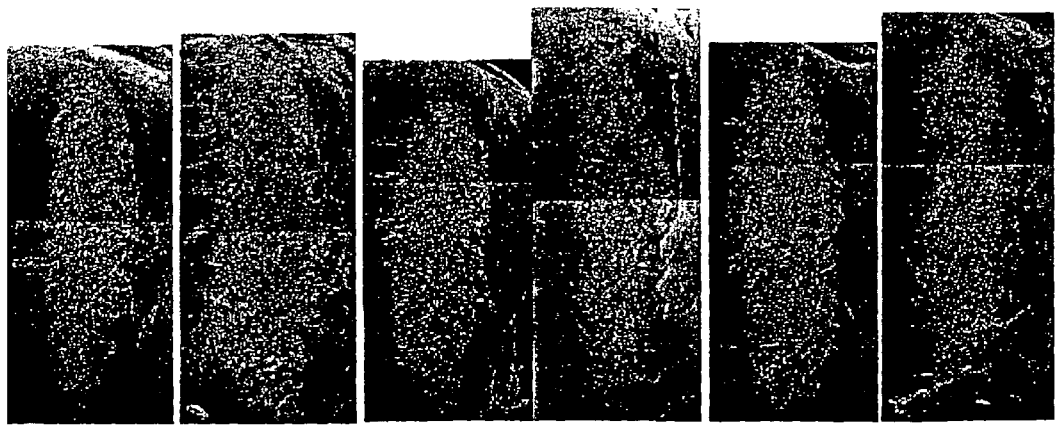
FIG. 15A is a set of scanning electron photomicrographs showing partially menisectomized rabbits given repeated intraarticular administration of a vehicle control (50% DMSO physiological saline solution) at 500 μL per day for 3 weeks beginning on the 7th day after the operation.
Figure 15B:
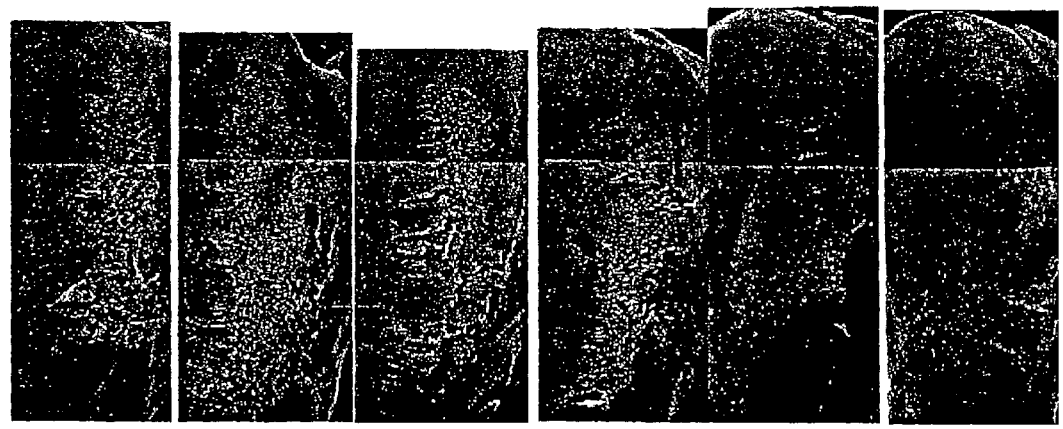
FIG. 15B is a set of scanning electron photomicrographs showing partially menisectomized rabbits given repeated intraarticular administration of compound A (3.0 mmol/L) at 500 μL per day for 3 weeks beginning on the 7th day after the operation.
Figure 16A:
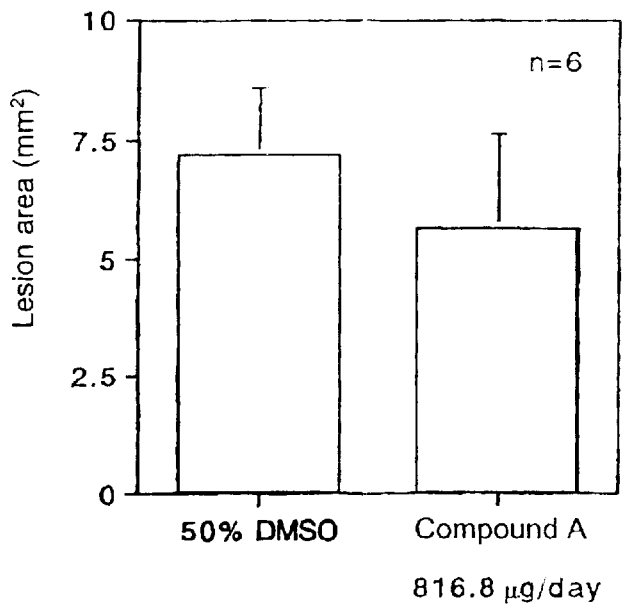
FIG. 16A, FIG. 16B and FIG. 16C are graphs showing the injured articular cartilage surface area from scanning electron photomicrographs of partially menisectomized rabbits given repeated intraarticular administration of compound A (3.0 mmol/L) and a vehicle control (50% DMSO physiological saline solution) at 500 μL per day for 3 weeks beginning on the 7th day after the operation.
Figure 16B:
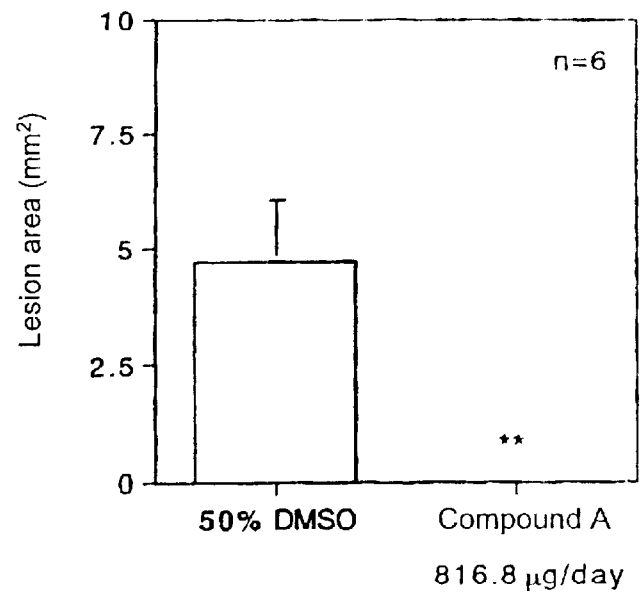
Figure 16C:
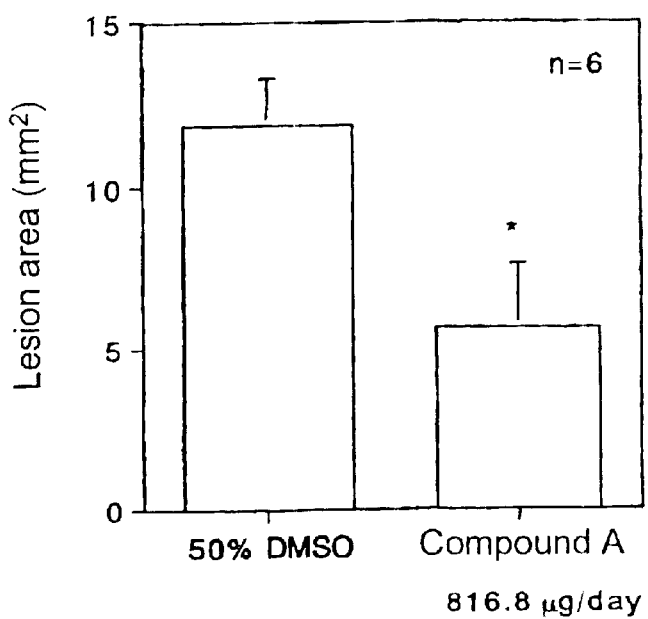

After post-fixation of the femoral distal section with 1% osmium solution (Wako Pure Chemical Industries), it was dipped in an increasing ethanol series for dehydrogenation, and then substituted with isoamyl acetate and subsequently dried with a critical point drying apparatus (Hitachi Co., Ltd.). The dried tissue surface was coated with gold using an ion sputter coating apparatus (Eiko Corp.), and the femoral condyle cartilage surface was observed using a scanning electron microscope (Hitachi Co., Ltd.) (FIGS. 15A and 15B). The area of the damaged sections of the articular cartilage in the electron photomicrograph was measured using IPAP image analysis software (Sumika Technoservice Co., Ltd.), and judged on the scale shown in Table 11 below. As shown in FIGS. 16A, 16B and 16C, the group administered compound A alone exhibited significantly smaller area of damage in the articular cartilage compared to the group administered the solvent alone, as judged from the medium grade lesion area and total lesion area.

TABLE 11

| Grade of lesion | Condition of articular cartilage surface |
| --- | --- |
| Mild | Destruction of cartilage surface and exposure of internal structure, but with a collagen fiber diameter of 10 μm or greater. |
| Medium | Exposed collagen fiber diameter of under 10 μm. |
| Severe | Loss of collagen fibers, exposure of calcified cartilage or subchondral bone. |

The proximal region of tibia was trimmed with a band saw (EXAKT Corp.) and then demineralized for 4 weeks with 20% EDTA-4Na solution (pH 7.4, Wako Pure Chemical Industries). The trimmed section was prepared into a paraffin block using an automatic embedding apparatus (Sakura Corp.) and paraffin (equivalent mixture of products by Kokusan Kagaku Corp. and Fisher Scientific Corp.). Here, a paraffin automatic dispensing embedding center (Miles Scientific Corp.) was used to fix each paraffin block in a tissue sample cassette (TISSUE-TEK Corp.)

The paraffin block was cut into 2 μm-thick sections using a microtome (Daiwa Optical Instruments Corp.) and microtome knife (Feather Co., Ltd.), and then attached onto slide glass (Matsunami Glass Corp.) and dried. After drying, the sections were dipped in xylene to remove the paraffin, and then dipped in a step dilution series from ethanol to water and stored in water. The sections were stained with 0.3% Safranin O (Merck Co., Ltd.), and then observed under a microscope (magnification: 10× object lens), and a histological score was assigned according to the following Table 12, which is a modification of the method of Kikuchi et al. (Osteoarthritis, Cartilage 4, 99–110, 1996).

TABLE 12

| Score | +1 | +2 | +3 | +4 |
| --- | --- | --- | --- | --- |
| Loss of superficial layer | Slight | Moderate | Focally severe | Extensively severe |
| Ulceration or erosion | Detectable | Moderate | Focally severe | Extensively severe |
| Fibrillation | Noticeable | Moderate | Marked | Extensive |
| Cluster formation* | 3–4 small or 1–2 medium | 5–6 small, 3–4 medium, or 1–2 large | 7 or more small, 5–6 medium, or 3–4 large | 7 or more medium or 5–6 large |
| Global assessment | Sum of above scores | | | |

*Small = 2–4 cells; medium = 5–8 cells; large = 9 or more cells

Figure 17A:
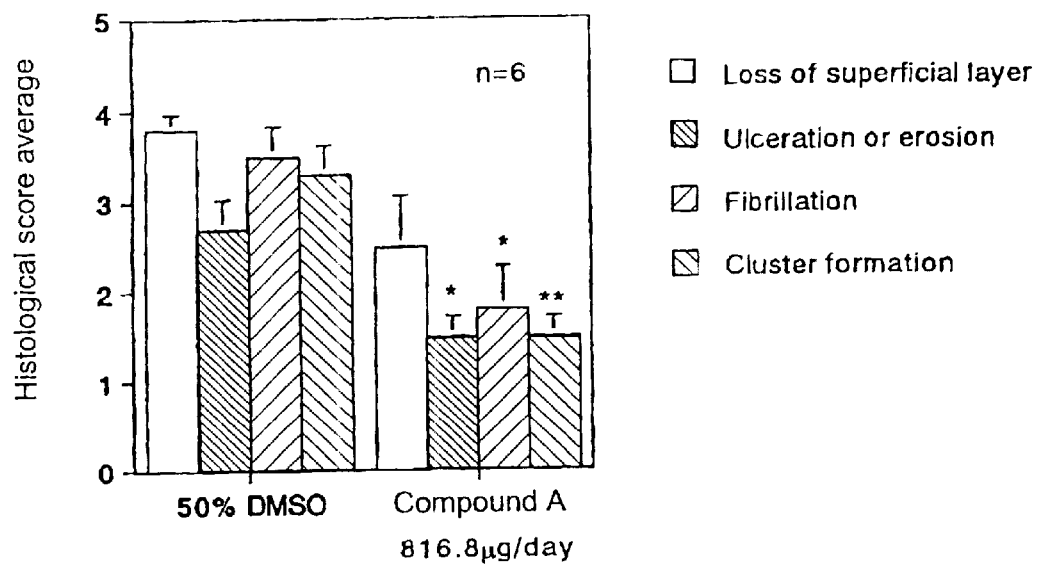
FIG. 17A and FIG. 17B are graphs showing the results of histological examination of 0.3% Safranin O stained samples of lesions in partial excisions from the articular crescents of rabbits given repeated intraarticular administration of compound A (3.0 mmol/L) and a vehicle control (50% DMSO physiological saline solution) at 500 μL per day for 3 weeks beginning on the 7th day after the operation.
Figure 17B:
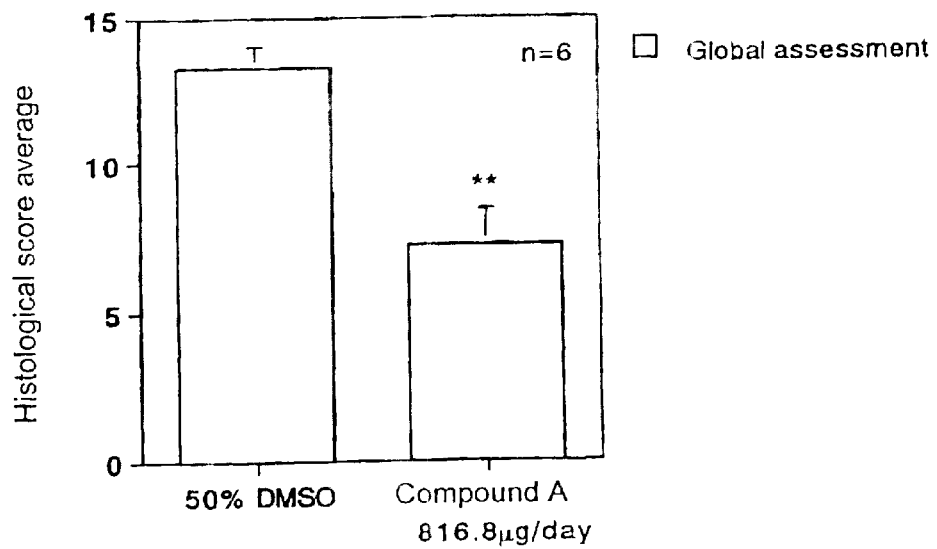

The group administered compound A alone had significantly lower total histological scores, except for the loss of superficial layer, compared to the group administered the solvent alone (FIGS. 17A and 17B). These experimental results confirmed that compound A exhibits a suppressing effect on cartilage degeneration in osteoarthritis and similar conditions.

Industrial Applicability

As explained above, the present invention provides chondrogenesis promoters and cartilage repair agents comprising as active ingredients indolin-2-one derivatives having specific structures, or their salts. These chondrogenesis promoters promote chondrogenesis in warm-blooded animals including humans, and are therefore expected to serve as excellent therapeutic agents for cartilage diseases such as rheumatoid arthritis or osteoarthritis, or cartilage defect due to injury.

In addition, the indolin-2-one derivatives with a chondrogenesis promoting effect according to the invention are also useful as reagents for biological, physical or chemical research on cartilage.

What is claimed is:

1. A method of producing a chondrocyte-containing composition comprising culturing a chondrocyte and/or a chondrocyte precursor in the presence of a compound represented by the general formula (I) or a salt thereof:

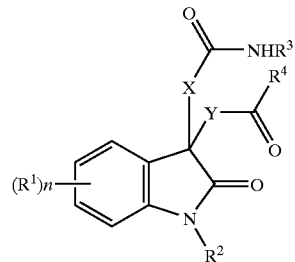

wherein
$R^1$ represents a halogen atom, a lower alkyl group, a lower alkoxy group, a hydroxyl group, a nitro group, a trifluoromethyl group, a lower alkylthio group, an acyl group, a carboxyl group, a mercapto group or an amino group with an optional substituent;
$R^2$ represents a hydrogen atom, a lower alkyl group with an optional substituent, a lower alkenyl group with an optional substituent, a lower alkynyl group with an optional substituent, a lower alkoxy group with an optional substituent, an acyl group with an optional substituent, an aryl group with an optional substituent or a heterocyclic group with an optional substituent;
$R^3$ represents a lower alkyl group with an optional substituent, a cycloalkyl group with an optional substituent, an aryl group with an optional substituent or a heterocyclic group with an optional substituent;
$R^4$ represents a hydrogen atom, a lower alkyl group with an optional substituent, an aryl group with an optional substituent, a heterocyclic group with an optional substituent, $-OR^5$, $-SR^5$ or $-NR^6NR^7$ wherein $R^5$, $R^6$ and $R^7$ may be the same or different and each represents a hydrogen atom, a lower alkyl group with an optional substituent, a cycloalkyl group with an optional substituent, an aryl group with an optional substituent, a heterocyclic group with an optional substituent, a lower alkoxy group or an amino group with an optional substituent, and $R^6$ and $R^7$ may together form a group represented by $-(CH_2)_m-$ or $-(CH_2)_l NR^8 (CH_2)_k-$ wherein k, l and m each represents an integer of 1–8 and $R^8$ represents a hydrogen atom or a lower alkyl group;
X and Y may be the same or different and each represents $-CH_2-$, $-NH-$ or $-O-$;
and n represents an integer of 0–4.

2. A method of producing a chondrocyte-containing composition according to claim 1, wherein
$R^1$ is a halogen atom, a lower alkyl group, a lower alkoxy group or a nitro group;
$R^2$ is a hydrogen atom, a lower alkyl group with an optional substituent, a lower alkenyl group with an optional substituent or an aryl group with an optional substituent;
$R^3$ is a lower alkyl group with an optional substituent, a cycloalkyl group with an optional substituent or an aryl group with an optional substituent;
$R^4$ is a lower alkyl group with an optional substituent, an aryl group with an optional substituent, a heterocyclic group with an optional substituent, $-OR^5$ or $-NR^6R^7$ wherein $R^5$, $R^6$ and $R^7$ are as previously defined;

X is —CH$_2$—, —NH— or —O—;
Y is —CH$_2$—or —NH—; and
n is 0 or 1.

3. A method of producing a chondrocyte-containing composition according to claim 1, wherein
R$^2$ is a lower alkyl group with an optional substituent which is optionally substituted with a halogen atom;
R$^3$ is an aryl group with an optional substituent;
R$^4$ is —NR$^6$R$^7$ wherein R$^6$ and R$^7$ may be the same or different and each represents a hydrogen atom or an aryl group with an optional substituent;
X and Y may be the same or different and each represents —CH$_2$— or —NH—; and
n is 0.

4. A method of producing a chondrocyte-containing composition according to claim 3, wherein
R$^2$ is a lower alkyl group substituted at the same carbon with two lower alkoxy groups which are optionally substituted with 1–5 halogen atoms or the group —O—Z—O— wherein Z represents a lower alkylene group optionally substituted with 1–10 halogen atoms;
R$^3$ is an aryl group which has a lower alkyl group or an amino group which amino group optionally has a lower alkyl group; and
R$^4$ is —NR$^6$R$^7$ wherein R$^6$ and R$^7$ may be the same or different and each represents a hydrogen atom or any aryl group which has a lower alkyl group or an amino group which amino group optionally has a lower alkyl group.

5. A method of producing a chondrocyte-containing composition according to claim 4, wherein
R$^2$ is a group represented by general formula (II):

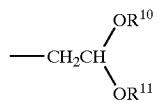

(II)

wherein R$^{10}$ and R$^{11}$ may be the same or different, and each represents a lower alkyl group optionally substituted with 1–5 halogen atoms, or general formula (III):

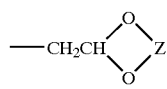

(III)

wherein Z represents a lower alkylene group optionally substituted with 1–10 halogen atoms.

6. A method of producing a chondrocyte-containing composition according to claim 5, wherein either or both R$^{10}$ and R$^{11}$ are lower alkyl groups with 1–5 halogen atoms.

7. A method of producing a chondrocyte-containing composition according to claim 5, wherein
R$^2$ is a 2,2-diethoxyethyl group, a 2,2-dimethoxyethyl group, a 2,2-diisopropoxyethyl group, a 2,2-bis(2-fluoroethoxy)ethyl group or a 2,2-bis(2-chloroethoxy)ethyl group;
X is —NH—; and
Y is —CH$_2$—.

8. A method of producing a chondrocyte-containing composition according to claim 5, wherein
R$^3$ is a 4-methylphenyl group;
X is —NH—; and
Y is —CH$_2$—.

9. A method of producing a chondrocyte-containing composition according to claim 5, wherein
R$^4$ is —NHR$^7$ wherein R$^7$ is a 4-methylphenyl group, a 4-ethylphenyl group or a 4-(N,N-dimethylamino)phenyl group;
X is —NH—; and
Y is —CH$_2$—.

10. A method of producing a chondrocyte-containing composition according to claim 5, wherein the combination of R$^2$, R$^3$ and R$^4$ is any of the following:
R$^2$ is a 2,2-diethoxyethyl group, R$^3$ is a 4-methylphenyl group and R$^4$ is —NHR$^7$ wherein R$^7$ is a 4-methylphenyl group;
R$^2$ is a 2,2-diethoxyethyl group, R$^3$ is a 4-methylphenyl group and R$^4$ is —NHR$^7$ wherein R$^7$ is a 4-ethylphenyl group;
R$^2$ is a 2,2-diethoxyethyl group, R$^3$ is a 4-methylphenyl group and R$^4$ is —NHR$^7$ wherein R$^7$ is a 4-(N,N-dimethylamino)phenyl group;
R$^2$ is a 2,2-dimethoxyethyl group, R$^3$ is a 4-methylphenyl group and R$^4$ is —NHR$^7$ wherein R$^7$ is a 4-methylphenyl group;
R$^2$ is a 2,2-diisopropoxyethyl group, R$^3$ is a 4-methylphenyl group and R$^4$ is —NHR$^7$ wherein R$^7$ is a 4-methylphenyl group;
R$^2$ is a 2,2-bis(2-fluoroethoxy)ethyl group, R$^3$ is a 4-methylphenyl group and R$^4$ is —NHR$^7$ wherein R$^7$ is a 4-methylphenyl group; or
R$^2$ is a 2,2-bis(2-chloroethoxy)ethyl group, R$^3$ is a 4-methylphenyl group and R$^4$ is —NHR$^7$ wherein R$^7$ is a 4-methylphenyl group.

11. A method of producing a chondrocyte-containing composition according to claim 1, wherein said culturing is performed ex-vivo.

12. A method of producing a chondrocyte-containing composition according to claim 1, wherein said chondrocyte precursor is an undifferentiated mesenchymal cell.

13. A method of producing a chondrocyte-containing composition according to claim 1, wherein said chondrocyte-containing composition comprises an extracellular matrix.

14. A method of producing a chondrocyte-containing composition according to claim 1, wherein said chondrocyte-containing composition is intended for chondrocyte transplantation.

15. A method of producing a chondrocyte-containing composition according to claim 14, wherein said chondrocyte transplantation is autogenous chondrocyte transplantation.

16. A chondrocyte-containing composition obtained by the method according to claim 1.

17. A chondrocyte-containing composition obtained by the method according to claim 11.

18. A chondrocyte-containing composition obtained by the method according to claim 12.

19. A chondrocyte-containing composition obtained by the method according to claim 13.

20. A chondrocyte-containing composition obtained by the method according to claim 14.

21. A chondrocyte-containing composition obtained by the method according to claim 15.

* * * * *